US009835625B2

(12) United States Patent
Eng (10) Patent No.: US 9,835,625 B2
(45) Date of Patent: Dec. 5, 2017

(54) METHODS AND COMPOSITIONS FOR DETECTION OF COWDEN SYNDROME (CS) AND CS-LIKE SYNDROME

(71) Applicant: The Cleveland Clinic Foundation, Cleveland, OH (US)

(72) Inventor: Charis Eng, Cleveland Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 14/947,851

(22) Filed: Nov. 20, 2015

(65) Prior Publication Data

US 2016/0209413 A1    Jul. 21, 2016

Related U.S. Application Data

(63) Continuation of application No. 13/445,688, filed on Apr. 12, 2012, now abandoned, which is a continuation of application No. 12/462,053, filed on Jul. 27, 2009, now abandoned.

(60) Provisional application No. 61/137,042, filed on Jul. 25, 2008.

(51) Int. Cl.
| | |
|---|---|
| C12Q 1/68 | (2006.01) |
| G01N 33/573 | (2006.01) |
| C12Q 1/32 | (2006.01) |
| C12Q 1/48 | (2006.01) |
| G01N 33/574 | (2006.01) |

(52) U.S. Cl.
CPC .............. *G01N 33/573* (2013.01); *C12Q 1/32* (2013.01); *C12Q 1/485* (2013.01); *C12Q 1/6883* (2013.01); *G01N 33/574* (2013.01); *C12Q 2600/156* (2013.01); *G01N 2333/90206* (2013.01); *G01N 2333/9121* (2013.01)

(58) Field of Classification Search
None
See application file for complete search history.

(56) References Cited

U.S. PATENT DOCUMENTS

| | | | |
|---|---|---|---|
| 8,163,493 | B2 | 4/2012 | Eng et al. |
| 8,206,910 | B2 | 6/2012 | Eng |
| 8,735,076 | B2 | 5/2014 | Eng et al. |
| 2003/0165895 | A1 | 9/2003 | Czerniak et al. |
| 2010/0092961 | A1 | 4/2010 | Eng |
| 2010/0159466 | A1 | 6/2010 | Eng |
| 2010/0255478 | A1 | 10/2010 | Eng |
| 2011/0014603 | A1 | 1/2011 | Eng et al. |
| 2012/0264631 | A1 | 10/2012 | Eng et al. |
| 2012/0322062 | A1 | 12/2012 | Eng et al. |

FOREIGN PATENT DOCUMENTS

| | | |
|---|---|---|
| WO | WO 2005/078139 A | 8/2005 |
| WO | WO 2005/118806 A | 12/2005 |
| WO | WO 2006/028967 A | 3/2006 |
| WO | WO 2008/002672 | 1/2008 |

OTHER PUBLICATIONS

Baysal, B.E., et al., "Mutations in *SDHD*, a Mitochondrial Complex II Gene, in Hereditary Paraganglioma," *Science*, 287:848-851 (Feb. 4, 2000).
Benn, D.E., et al., "Clinical Presentation and Penetrance of Pheochromocytoma/Paraganglioma Syndromes," *The Journal of Clinical Endocrinology & Metabolism*, 91(3):827-836 (2006; Online Nov. 29, 2005).
Cascon, A., et al., "G12S and H50R Variations are Polymorphisms in the *SDHD* Gene," *Genes, Chromosomes & Cancer*, 37:220-221 (2003).
Chung, J.-H., et al., "Nuclear-Cytoplasmic Partitioning of Phosphatase and Tensin Homologue Deleted on Chromosome 10 (PTEN) Differentially Regulates the Cell Cycle and Apoptosis," *Cancer Res.*, 65(18):8096-8100 (Sep. 15, 2005).
Eng, C., et al., "A Role for Mitochondrial Enzymes in Inherited Neoplasia and Beyond," *Nature Reviews Cancer*, 3:193-202 (Mar. 2003).
Eng, C., "*PTEN*: One Gene, Many Syndromes," *Human Mutation*, 22:183-198 (2003).
Ishii, T., et al., "A Mutation in the *SDHC* Gene of Complex II Increases Oxidative Stress, Resulting in Apoptosis and Tumorigenesis," *Cancer Res.*, 65(1):203-209 (Jan. 1, 2005).

(Continued)

*Primary Examiner* — Carla Myers
(74) *Attorney, Agent, or Firm* — Hamilton, Brook, Smith & Reynolds, P.C.

(57) ABSTRACT

In one aspect, the invention is directed to a method of detecting Cowden syndrome (CS) or CS-like syndrome in an individual comprising detecting the presence of a mutated succinate dehydrogenase B (SDHB), mutated succinate dehydrogenase D (SDHD) or combination thereof in the individual, wherein detection of a mutated SDHB, SDHD or a combination thereof indicates that the individual is positive for CS or CS-like syndrome. In another aspect, the invention is directed to a method of determining whether an individual is at risk for developing Cowden syndrome (CS) or CS-like syndrome comprising detecting the presence of a mutated succinate dehydrogenase B (SDHB), mutated succinate dehydrogenase D (SDHD) or combination thereof in the individual, wherein detection of a mutated SDHB, SDHD or a combination thereof indicates that the individual is at risk for developing for CS or CS-like syndrome. In yet another aspect, the invention is directed to an article of manufacture for detecting Cowden syndrome (CS) or Cowden-like syndrome in an individual, comprising one or more agents that detects mutated succinate dehydrogenase B (SDHB), mutated succinate dehydrogenase D (SDHD) or combination thereof in the individual, and instructions for use.

8 Claims, 6 Drawing Sheets

(56) References Cited

OTHER PUBLICATIONS

Koivunen, P., et al., "Inhibition of Hypoxia-inducible Factor (HIF) Hydroxylases by Citric Acid Cycle Intermediates Possible Links Between Cell Metabolism and Stabilization of HIF," *The Journal of Biological Chemistry*, 282(7):4524-4532 (Feb. 16, 2007).

Kryukov, G.V., et al., "Most Rare Misense Alleles are Deleterious in Humans: Implications for Complex Disease and Association Studies," *The American Journal of Human Genetics*, 80:727-739 (Apr. 2007).

Kytölä, S., et al., "Alterations of the *SDHD* Gene Locus in Midgut Carcinoids, Merkel Cell Carcinomas, Pheochromocytomas, and Abdominal Paragangliomas," *Genes, Chromosomes & Cancer*, 34:325-332 (2002).

Launonen, V., et al., "Inherited Susceptibility to Uterine Leiomyomas and Renal Cell Cancer," *PNAS*, 98(6):3387-3392 (Mar. 13, 2001).

Lee, S.-R., et al., "Reversible Inactivation of the Tumor Suppressor PTEN by $H_2O_2$," *The Journal of Biochemical Chemistry* 277(23):20336-20342 (Jun. 7, 2002).

Liaw, D., et al., "Germline Mutations of the *PTEN* Gene in Cowden Disease, an Inherited Breast and Thyroid Cancer Syndrome," *Nature Genetics*, 16:64-67 (May 1997).

Marsh, D.J., et al., "Mutation Spectrum and Genotype-phenotype Analyses in Cowden Disease and Bannayan-Zonana Syndrome, Two Hamartoma Syndromes with Germline *PTEN* Mutation," *Human Molecular Genetics*, 7(3):507-515 (1998).

McWhinney, S.R., et al., "Large Germline Deletions of Mitochondrial Complex II Subunits *SDHB* and *SDHD* in Hereditary Paraganglioma," *The Journal of Clinical Endocrinology & Metabolism*, 89(11):5694-5699 (2004).

Mutter, G.L., et al., "Altered PTEN Expression as a Diagnostic Marker for the Earliest Endometrial Precancers," *Journal of National Cancer Institute*, 92(11):924-931 (Jun. 7, 2000).

Nelen, M.R., et al., "Localization of the Gene for Cowden Disease to Chromosome 10q22-23," *Nature Genetics*, 13:114-116 (May 1996).

Neumann, H.P.H., et al., "Germ-line Mutations in Nonsyndromic Pheochromocytoma," *N. Engl. J. Med.*, 346(19):1459-1466 (May 9, 2002).

Ni, Y., et al., "Germline Mutations and Variants in the Succinate Dehydrogenase Genes in Cowden and Cowden-like Syndromes," *The American Journal of Human Genetics*, 83:261-268 (Aug. 8, 2008).

Perren, A., et al., "Absence of Somatic *SDHD* Mutations in Sporadic Neuroendocrine Tumors and Detection of Two Germline Variants in Paraganglioma Patients," *Oncogene*, 21:7605-7608 (2002).

Selak, M.A., et al., "Succinate Links TCA Cycle Dysfunction to Oncogenesis by Inhibiting HIF-α Prolyl Hydroxylase," *Cancer Cell*, 7:77-85 (Jan. 2005).

Slane, B.G., et al., "Mutation of Succinate Dehydrogenase Subunit C Results in Increased $O_2$ Oxidative Stress, and Genomic Instability," *Cancer Res.*, 66(15):7615-7620 (Aug. 1, 2006).

Stambolic, V., et al., "High Incidence of Breast and Endometrial Neoplasia Resembling Human Cowden Syndrome in $pten^{+/-}$ Mice," *Cancer Research*, 60:3605-3611 (Jul. 1, 2000).

Stambolic, V., et al., "Negative Regulation of PKB/Akt-Dependent Cell Survival by the Tumor Suppressor PTEN," *Cell*, 95:29-39 (Oct. 2, 1998).

Tang, Y. and Eng, C., "PTEN Autoregulates Its Expression by Stabilization of p53 in a Phosphatase-Independent Manner," *Cancer Research*, 66(2):736-742 (Jan. 15, 2006).

Vanharanta, S., et al., "Early-Onset Renal Cell Carcinoma as a Novel Extraparaganglial Component of *SDHB*-Associated Heritable Paraganglioma," *Am. J. Hum. Genet.*, 74:153-159 (2004; electronically Dec. 18, 2003).

Weng, L.-P., et al., "PTEN Blocks Insulin-mediated ETS-2 Phosphorylation Through MAP Kinase, Independently of the Phosphoinositide 3-kinase Pathway," *Human Molecular Genetics*, 11(15):1687-1696 (2002).

Zbuk, K.M and Eng, C., "Cancer Phenomics: *RET* and *PTEN* as Illustrative Models," *Nature Reviews Cancer*, 7:35-45 (Jan. 2007).

Zhou, X.P., et al., "Germline PTEN Promoter Mutations and Deletions in Cowden/Bannayan-Riley-Ruvalcaba Syndrome Result in Aberrant PTEN Protein and Dysregulation of the Phosphoinositol-3-Kinase/Akt Pathway," *Am. J. Hum. Genet,*. 73(2):404-411 (Aug. 2003; EPub Jul. 3, 2003).

Zundel, W., et al., "Loss of *PTEN* Facilitates HIF-1-mediated Gene Expression," *Genes & Development*, 14:391-396 (2000).

Bonneau, D., et al., "Mutations of the Human PTEN Gene," *Hum. Mutat.*, 16:109-122 (2000).

Carethers, J.M., et al., "Absence of PTEN/MMAC1 Germ-Line Mutations in Sporadic Bannayan-Riley-Ruvalcaba Syndrome," *Cancer Res.*, 58:2724-2726 (Jul. 1, 1998).

Drysdale, C.M., et al., "Complex Promoter and Coding Region $\beta_2$-Adrenergic Receptor Haplotypes Alter Receptor Expression and Predict in vivo Responsiveness," *Proc. Natl. Acad. Sci. U.S.A.*, 97(19):10483-10488 (Sep. 12, 2000).

Eng, C., "Will the Real Cowden Syndrome Please Stand Up: Revised Diagnostic Criteria," *J. Med. Genet.*, 37:828-830 (2000).

Greenwood, T.A., et al., "Promoter and Intronic Variants Affect the Transcriptional Regulation of the Human Dopamine Transporter Gene," *Genomics*, 82:511-519 (2003).

Haiman, C.A., et al., "Common Genetic Variation at PTEN and Risk of Sporadic Breast and Prostate Cancer," *Cancer Epidemiol. Biomarkers Prev.*, 15(5):1021-1025 (May 2006).

Hamilton. J.A., et al., "The Expression Profile for the Tumour Suppressor Gene PTEN and Associated Polymorphic Markers," *Br. J. Cancer*, 82(10):1671-1676 (2000).

Kleinjan, D.A., et al., "Long-Range Control of Gene Expression: Emerging Mechanisms and Disruption in Disease," *Am. J. Hum. Genet.*, 76:8-32 (2005; electronically Nov. 17, 2004).

Loffeld, A., et al., "Epidermal Naevus in Proteus Syndrome Showing Loss of Heterozygosity for an Inherited PTEN Mutation," *Br. J. Dermatol.*, 154:1194-1198 (2006).

Maehama, T. and Dixon, J.E., "The Tumor Suppressor, PTEN/MMAC1, Dephosphorylates the Lipid Second Messenger, Phosphatidylinositol 3,4,5-Trisphosphate," *J. Biol. Chem.*, 273(22):13375-13378 (1998).

Marsh, D.J., et al.. "PTEN mutation Spectrum and Genotype-Phenotype Correlations in Bannayan-Riley-Ruvalcaba Syndrome Suggest a Single Entity with Cowden Syndrome," *Hum. Mol. Genet.*, (8)8:1461-1472 (1999).

Pilarski, R. and Eng, C., "Will the Real Cowden Syndrome Please Stand Up (Again)? Expanding Mutational and Clinical Spectra of the PTEN Hamartoma Tumour Syndrome", *J. Med. Genet.*, 41:323-326 (2004).

Smith, J.M., et al., "Germline Mutation of the Tumour Suppressor PTEN in Proteus Syndrome," *J. Med. Genet.*, 39:937-940 (2002).

Yu,C., et al., "Functional Haplotypes in the Promoter of Matrix Metalloproteinase-2 Predict Risk of the Occurrence and Metastasis of Esophageal Cancer," *Cancer Res.*, 64:7622-7628 (Oct. 15, 2004).

Zhang, L., et al.. "Association of the Phosphatase and Tensin Homolog Gene (PTEN) with Smoking Initiation and Nicotine Dependence", *Am. J. Med. Genet. Part B* (*Neuropsychiatr. Genet.*), 141B:10-14 (2006).

Zhou, X., et al., "Association of Germline Mutation in the PTEN Tumour Suppressor Gene and Proteus and Proteus-like Syndromes," *Lancet*, 358:210-211 (2001).

6th edition of the American Joint Committee on Cancer (AJCC) Cancer Staging Manual (Greene, F., et al., eds. AJCC Cancer Staging Manual, 6th edition. New York: Springer-Verlag; (2002)).

A Conference on Nonparametric Inference and Probability with Applications to Science (Honoring Michael Woodroofe), Ann Arbor, Michigan, 2005). The R package (http://www.r-project.org).

Ada-Nguema, A. S., et al., "The Small GTPase R-Ras Regulates Organization of Actin and Drives Membrane Protrusions Through the Activity of PLCε," *Journal of Cell Science*, 119:1307-1319 (2006).

Aldred, M.A., et al., "Papillary and Follicular Thyroid Carcinomas Show Distinctly Different Microarray Expression Profiles and can be Distinguished by a Minimum of Five Genes," *J Clin Onco.* 22(17):3531-3539 (2004).

(56) References Cited

OTHER PUBLICATIONS

Aldred, M.A., et al., "Peroxisome Proliferator-activated Receptor Gamma is Frequently Downregulated in a Diversity of Sporadic Nonmedullary Thyroid Carcinomas," *Oncogene* 22:3412-3416 (2003).
Allinen, M., et al., "Molecular Characterization of the Tumor Microenvironment in Breast Cancer," *Cancer Cell* 6:17-32 (2004).
Alvarez-Garcia, I., et al., "MicroRNA Functions in Animal Development and Human Disease," *Development* 132(21):4653-4662 (2005).
Antoniou, A. C., et al., "A Comprehensive Model for Familial Breast Cancer Incorporating BRCA1, BRCA2 and Other Genes," *British Journal of Cancer*, 86:76-83 (2002).
Appelhoff, R.J., et al., "Differential Function of the Prolyl Hydorxylases PHD1, PHD2, and PHD3 in the Regulation of Hypoxia-inducible Factor," *J of Bio Chem* 279(37):38458-38465 (2004).
Argraves, W.S., et al., "Fibulins: Physiological and Disease Perspectives," *EMBO Reports* 4(12):1127-1131 (2003).
Auer, H., et al., "Chipping Away at the Chip Bias: RNA Degradation in Microarray Analysis," *Nature Genetics* 35(4):292-293 (2003).
Barclay, W. W., et al., "A System for Studying Epithelial-Stromal Interactions Reveals Distinct Inductive Abilities of Stromal Cells from Benign Prostatic Hyperplasia and Prostate Cancer," *Endocrinology*, 146(1):13-18 (Jan. 2005).
Berezikov, E., et al., "Approaches to MicroRNA Discovery," *Nature Genetics* 38:S2-S7 (2006).
Bhowmick, N.A., et al., "Stromal Fibroblasts in Cancer Initiation and Progression," *Nature* 432:332-337 (2004).
Bissell, M.J., et al., "The Influence of Extracellular Matrix on Gene Expression: Is Structure the Message?," *J. Cell Sci. Suppl* 8:327-343 (1987).
Bockmühl, U., et al., "Chromosomal Alterations During Metastasis Formation of Head and Neck Squamous Cell Carcinoma," *Genes, Chromosomes & Cancers* 33:29-35 (2002).
Bockmühl, U., MD, et al., "Genomic Alterations Associated with Malignancy in Head and Neck Cancer," *Head & Neck* 20:145-151 (1998).
Boucheix, C., et al., "Tetraspanins and Malignancy," *Expert Reviews in Molecular Medicine*:1-17 (2001).
Braakhuis, B.J.M., et al., "A Genetic Explanation of Slaughter's Concept of Field Cancerization: Evidence and Clinical Implications," *Cancer Research* 63:1727-1730 (2003).
Braakhuis, B.J.M., et al., "Expanding Fields of Genetically Altered Cells in Head and Neck Squamous Carcinogenesis," *Seminars in Cancer Biology* 15:113-120 (2005).
Calin, G.A., MD, PhD, et al., "A MicroRNA Signature Associated with Prognosis and Progression in Chronic Lymphocytic Leukemia," *N Engl J Med* 353(17):1793-1801 (2005).
Canobbio, I., et al., "Altered Cytoskeleton Organization in Platelets from Patients with MYH9-related Disease," *J of Thrombosis and Haemostasis* 3:1026-1035 (2005).
Cerutti, J.M., et al., "A Preoperative Diagnostic Test that Distinguishes Benign from Malignant Thyroid Carcinoma Based on Gene Expression," *The Journal of Clinical Investigation* 113(8): 1234-1242 (2004).
Chen, C.-Z., Ph.D., "MicroRNAs as Oncogenes and Tumor Suppressors," *N Engl J Med* 353:1768-1771 (2005).
Chen, E.I., et al., "Maspin and Tumor Metastasis," *IUBMB Life* 58(1):25-29 (2006).
Chen, S.-L., et al., "p53 is a Regulator of the Metastasis Suppressor Gene Nm23-H1," *Molecular Carcinogenesis*, 36:204-214 (2003).
Climent, J., et al., "Genomic Loss of 18p Predicts an Adverse Clinical Outcome in Patients with High-Risk Breast Cancer," *Clinical Cancer Research* 8:3863-3869 (2002).
Cocco, L., et al.. "Nuclear Phospholipase C β1, Regulation of the Cell Cycle and Progression of Acute Myeloid Leukemia," *Advan. Enzyme Regul* 45:126-135 (2005).
Condon, M.S., "The Role of the Stromal Microenvironment in Prostate Cancer," *Seminars in Cancer Biology* 15:132-137 (2005).

Cornélis, F., et al., "New Susceptibility Locus for Rheumatoid Arthritis Suggested by a Genome-Wide-Linkage Study," *Proc. Natl. Acad. Sci. USA* 95:10746-10750 (1998).
Cuneo, A., et al., "Acquired Chromosome 11q Deletion Involving the Ataxia Teleangiectasia Locus in B-Cell Non-Hodgkin's Lymphoma: Correlation with Clinicobiologic Features," *J of Clin Oncology* 18(13):2607-2614 (2000).
Dacic, S., MD, et al., "Patterns of Allelic Loss of Synchronous Adenocarcinomas of the Lung," *Am J Surg Pathol* 29(7):897-902 (2005).
Dai, M.-S., et al., "The Effects of the Fanconi Anemia Zinc Finger (FAZF) on Cell Cycle, Apoptosis, and Proliferation are Differentiation Stage-specific," *The J. of Biological Chem* 277(29):26327-26334 (2002).
Debies, M.T., et al., "Genetic Basis of Human Breast Cancer Metastasis," *J of Mammary Gland Biology and Neoplasia* 6(4):441-451 (2001).
Denison, S.R., et al., "Characterization of FRA6E and Its Potential Role in Autosomal Recessive Juvenile Parkinsonism and Ovarian Cancer," *Genes, Chromosomes & Cancer* 38:40-52 (2003).
Edlund, M., et al., "Modulation of Prostate Cancer Growth in Bone Microenvironments," *Journal of Cellular Biochemistry* 91:686-705 (2004).
Eissa, S., et al., "Multivariate Analysis of DNA ploidy, P53, c-erbB-2 Proteins, EGFR, and Steroid Hormone Receptors for Short Term Prognosis in Breast Cancer," *Anticancer Research*, 17(4B):3091-3098 (Jul.-Aug. 1997).
Ellsworth, R.E., et al., "Allelic Imbalance in Primary Breast Carcinomas and Metastatic Tumors of the Axillary Lymph Nodes," *Molecular Cancer Research* 3(2):71-77 (2005).
Fagin, J.A., "Perspective: Lessons Learned from Molecular Genetic Studies of Thyroid Cancer-Insights into Pathogenesis and Tumor-Specific Therapeutic Targets," *Endocrinology* 143(6):2025-2028 (2002).
Farahati, J., et al., "Changing Trends of Incidence and Prognosis of Thyroid Carcinoma in Lower Franconia, Germany, from 1981-1995," *Thyroid* 14(2):141-147 (2004).
Forastiere, A., M.D., et al., "Head and Neck Cancer," *N Engl J Med* 345(26):1890-1900 (2001).
Fukino, K., et al.. "Combined Total Genome Loss of Heterozygosity Scan of Breast Cancer Stroma and Epithelium Reveals Multiplicity of Stromal Targets," *Cancer Research* 64:7231-7236 (2004).
Fukino, K., et al., "Genomic Instability Within Tumor Stroma and Clinicopathological Characteristics of Sporadic Primary Invasive Breast Carcinoma," *JAMA* 297(19):2103-2111 (2007).
Gallagher, W.M., et al., "Human Fibulin-4: Analysis of its Biosynthetic Processing and mRNA Expression in Normal and Tumour Tissues," *FEBS Letters* 489:59-66 (2001).
Gasco, M., et al., "TP53 Mutations in Familial Breast Cancer: Functional Aspects," *Human Mutation*, 21:301-306 (2003).
Ginzinger, D.G., et al., "Measurement of DNA Copy Number at Microsatellite Loci Using Quantitative PCR Analysis," *Cancer Research* 60:5405-5409 (2000).
Gort, M., et al., "Improvement of Best Practice in Early Breast Cancer: Actionable Surgeon and Hospital Factors," *Breast Cancer Res Treat* 102:219-226 (2007).
Götte, K., et al., "Intratumoral Genomic Heterogeneity in Advanced Head and Neck Cancer Detected by Comparative Genomic Hybridization," *Current Research in Head and Neck Cancer* 62:38-48 (2005).
Grünweller, A., et al., "RNA Interferences as a Gene-Specific Approach for Molecular Medicine," *Current Medicinal Chemistry* 12:3143-3161 (2005).
Hainaut, P., and Hollstein, M., "p53 and Human Cancer: The First Ten Thousand Mutations," *Advances in Cancer Research*, 77:81-137 (2000).
Hartikainen, J.M., et al., "An Autosome-Wide Scan for Linkage Disequilibrium-Based Association in Sporadic Breast Cancer Cases in Eastern Finland: Three Candidate Regions Found," *Cancer Epidemiology, Biomarkers & Prevention* 14(1):75-80 (2005).
Hartman, A.-R., and Ford, J. M., "BRCA1 Induces DNA Damage Recognition Factors and Enhances Nucleotide Excision Repair," *Nature Genetics*, 32:180-184 (Sep. 2002).

(56) References Cited

OTHER PUBLICATIONS

Hayward, S. W., et al., "Malignant Transformation in a Nontumorigenic Human Prostatic Epithelial Cell Line," *Cancer Research*, 61:8135-8142 (Nov. 15, 2001).
He, H., et al., "The Role of MicroRNA Genes in Papillary Thyroid Carcinoma," *PNAS* 102(52):19075-19080 (2005).
Hill, R., et al., "Selective Evolution of Stromal Mesenchyme with p53 Loss in Response to Epithelial Tumorigenesis," *Cell* 123:1001-1011 (2005).
Hoatlin, M.E., et al., "A Novel BTB/POZ Transcriptional Repressor Protein Interacts with the Fanconi Anemia Group C Protein and PLZF," *Blood* 94:3737-3747 (1999).
Hollstein, M., et al., "p53 Mutations in Human Cancers," *Science*, 253:49-53 (Jul. 5, 1991).
Horváth, B., MD, et al., "Expression of ETS-1 Transcription Factor in Human Head and Neck Squamous Cell Carcinoma and Effect of Histamine on Metastatic Potential of Invasive Tumor Through the Regulation of Expression of ETS-1 and Matrix Metalloproteinase-3," *Head & Neck* 27:585-596 (2005).
Hu, M., et al., "Distinct Epigenetic Changes in the Stromal Cells of Breast Cancers," *Nature Genetics* 37(8):899-905 (2005).
Huang, Q., et al., "Genetic Differences Detected by Comparative Genomic Hybridization in Head and Neck Squamous Cell Carcinomas from Different Tumor Sites: Construction on Oncogenetic Trees for Tumor Progression," *Genes, Chromosomes & Cancer* 34:224-233 (2002).
Hunter, K.D., et al., "Profiling Early Head and Neck Cancer," *Cancer* 5:127-135 (2005).
Hussain, S., et al., "Direct Interaction of FANCD2 with BRCA2 in DNA Damage Response Pathways," *Human Molecular Genetics* 13(12):1241-1248 (2004).
Iorio, M.V., et al., "MicroRNA Gene Expression Deregulation in Human Breast Cancer," *Cancer Res* 65(16):7065-7070 (2005).
Jang, S.J., et al., "Multiple Oral Squamous Epithelial Lesions: Are They Genetically Related?," *Oncogene* 20:2235-2242 (2001).
Jiang, J., et al., "Real-time Expression Profiling of microRNA Precursors in Human Cancer Cell Lines", *Nucleic Acids Res.*, 33(17) : 5394-5403 (2005).
Jukkola, T., et al., "*Drapc1* Expression During Mouse Embryonic Development," *Gene Expression Patterns* 4:755-762 (2004).
Kastan, M. B., and Bartek, J., "Cell-Cycle Checkpoints and Cancer," *Nature*, 432:316-323 (Nov. 18, 2004).
Kebebew, E., MD, "Diagnostic and Prognostic Value of Angiogenesis-Modulating Genes in Malignant Thyroid Neoplasms," *Surgery* 138:1102-1110 (2005).
Khanna, K.K., et al., "ATM and Genome Maintenance: Defining Its Role in Breast Cancer Susceptibility," *J. of Mammary Gland Biology and Neoplasia* 9(3):247-262 (2004).
Kimura, E.T., et al., "High Prevalence of *BRAF* Mutations in Thyroid Cancer: Genetic Evidence for Constitutive Activation of the RET/PTC-RAS-BRAF Signaling Pathway in Papillary Thyroid Carcinoma," *Cancer Research* 63:1454-1457 (2003).
Kraiem, Z., et al., "Matrix Metalloproteinases and the Thyroid," *Thyroid* 10(12):1061-1069 (2000).
Krubasik, D., et al., "Absence of p300 Induces Cellular Phenotypic Changes Characteristic of Epithelial to Mesenchyme Transition," *British Journal of Cancer* 94:1326-1332 (2006).
Krützfeldt, J., et al., "Silencing of microRNAs in vivo with 'antagomirs'," *Nature* 438:685-689 (2005).
Kurose, K., et al., "Frequent Somatic Mutations in *PTEN* and TP53 are Mutually Exclusive in the Stroma of Breast Carcinomas," *Nature Genetics* 32:355-357 (2002).
Kurose, K., et al., "Genetic Model of Multi-Step Breast Carcinogenesis Involving the Epithelium and Stroma: Clues to Tumour-Microenvironment Interactions," *Human Molecular Genetics* 10(18):1907-1913 (2001).
Lagos-Quintana, M., et al., "New MicroRNAs from Mouse and Human," *RNA* 9:175-179 (2003).
Leng, K., et al., "Refined Characterization of Head and Neck Squamous Cell Carcinomas Expressing a Seemingly Wild-type p53 Protein," *J Oral Pathol Med* 35:19-24 (2006).
Liu, C.-G., et al., "An Oligonucleotide Microchip for Genome-wide MicroRNA Profiling in Human and Mouse Tissues," *PNAS* 101(26):9740-9744 (2004).
Lu, J., et al., "MicroRNA Expression Profiles Classify Human Cancers," *Nature* 435:834-838 (2005).
Maffini, M. V., et al., "Stromal Regulation of Neoplastic Development: Age-Dependent Normalization of Neoplastic Mammary Cells by Mammary Stroma," *American Journal of Pathology* 167(5):1405-1410 (Nov. 2005).
Marsh, D.J., et al.. "Differential Loss of Heterozygosity in the Region of the Cowden Locus Within 10q22-23 in Follicular Thyroid Adenomas and Carcinomas," *Cancer Research* 57:500-503 (1997).
Martin, A.-M., et al., "Germline TP53 Mutations in Breast Cancer Families with Multiple Primary Cancers: Is TP53 a Modifier of BRCA1?," *J. Med. Genet.*, 40(/e34):1-6 (2003).
Matrisian, L. M., et al., "Epithelial-Stromal Interactions and Tumor Progression: Meeting Summary and Future Directions," *Cancer Research*, 61:3844-3846 (May 1, 2001).
McCawley, L.J., et al., "Tumor Progression: Defining the Soil Round the Tumor Seed," *Current Biology* 11:R25-R27 (2001).
Miska, E.A., "How MicroRNAS Control Cell Division, Differentiation and Death," *Current Opinion in Genetics & Development* 15:563-568 (2005).
Moinfar, F., et al., "Concurrent and Independent Genetic Alterations in the Stromal and Epithelial Cells of Mammary Carcinoma: Implications for Tumorigenesis," *Cancer Research* 60:2562-2566 (2000).
Mueller, M.M., et al., "Friends or Foes—Bipolar Effects of the Tumour Stroma in Cancer," *Cancer* 4:839-849 (2004).
Murakami, Y., et al., "Comprehensive Analysis of MicroRNA Expression Patterns in Hepatocellular Carcinoma and Non-Tumorous Tissues," *Oncogene* 25:2537-2545 (2006).
Naguibneva, I., et al., "The MicroRNA miR-181 Targets the Homeobox Protein Hox-A11 During Mammalian Myoblast Differentiation," *Nature Cell Biology* 8(3):278-284 (2006).
Narod, S. A., and Foulkes, W. D., "BRCA1 and BRCA2: 1994 and Beyond," *Nature*, 4:665-676 (Sep. 2004).
Nelson, H.H., et al., "TP53 Mutation, Allelism and Survival in Non-small Cell Lung Cancer," *Carcinogenesis* 26(10):1770-1773 (2005).
Nigro, J.M., et al., "Technical Advance Detection of 1p and 19q Loss in Oligodendroglioma by Quantitative Microsatellite Analysis, a Real-Time Quantitative Polymerase Chain Reaction Assay," *American Journal of Pathology* 158(4):1253-1262 (2001).
Overgaard, J., et al., "TP53 Mutation is an Independent Prognostic Marker for Poor Outcome in Both Node-negative and Node-positive Breast Cancer," *Acta Oncologica* 39:(3)327-333 (2000).
Passler, C., et al., "Prognostic Factors of Papillary and Follicular Thyroid Cancer: Differences in an Iodine-Replete Endemic Goiter Region," *Endocrine-Related Cancer* 11:131-139 (2004).
Patocs, A., et al., "Breast-Cancer Stromal Cells with TP53 Mutations and Nodal Metastases," *The New England Journal of Medicine.*, 357(25):2543-2551 (Dec. 20, 2007).
Perez-Ordoñez, B., et al., "Molecular Biology of Squamous Cell Carcinoma of the Head and Neck," *J Clin Pathol* 59:445-453 (2006).
Pharoah, P. D. P., et al., "Somatic Mutations in the p53 Gene and Prognosis in Breast Cancer: A Meta-Analysis," *British Journal of Cancer*, 80(12):1968-1973 (1999).
Poy, M.N., et al., "A Pancreatic Islet-Specific MicroRNA Regulates Insulin Secretion," *Nature* 432:226-230 (2004).
Radmacher, M.D., et al., "A Paradigm for Class Prediction Using Gene Expression Profiles," *Journal of Computational Biology* 9(3):505-511 (2002).
Ricci, F., et al., "Stromal Responses to Carcinomas of the Pancreas," *Cancer Biology & Therapy* 4(3):302-307 (2005).
Ries, L.A.G., et al., "Surveillance Epidemiology and End Results," *Cancer Statistics Review National Cancer Institute* 1975-2003 (2006).

(56) References Cited

OTHER PUBLICATIONS

Rio, P.G., et al., "Loss of Heterozygosity of BRCA1, BRCA2 and ATM Genes in Sporadic Invasive Ductal Breast Carcinoma," *International Journal of Oncology* 13:849-853 (1998).
Rosenquist, T.A., et al., "The Novel DNA Glycosylase, NEIL1 Protects Mammalian Cells from Radiation-mediated Cell Death," *DNA Repair* 2:581-591 (2003).
Rosenthal, E., et al., "Elevated Expression of TGF-β1 in Head and Neck Cancer-Associated Fibroblasts," *Molecular Carcinogenesis* 40:116-121 (2004).
Sarquis, M.S., et al., "High Frequency of Loss of Heterozygosity in Imprinted, Compared with Nonimprinted, Genomic Regions in Follicular Thyroid Carcinomas and Atypical Adenomas," *The Journal of Clinical Endocrinology & Metabolism* 91(1):262-269 (2006).
Schedin, P., et al., "Multistep Tumorigenesis and the Microenvironment," *Breast Cancer Res* 6:93-101 (2004).
Schulte, K.-M., et al., "Activin A and Activin Receptors in the Human Thyroid: A Link to the Female Predominance of Goiter?," *Horm Metab Res* 32:390-400 (2000).
Schulte, K.-M., et al., "Activin A and Activin Receptors in Thyroid Cancer," *Thyroid* 11(1):3-14 (2001).
Segev, D.L., et al., "Molecular Pathogenesis of Thyroid Cancer," *Surgical Oncology* 12:69-90 (2003).
Segev, D.L., M.D., et al., "Beyond the Suspicious Thyroid Fine Needle Aspirate A Review," *Acta Cytol* 47:709-722 (2003).
Shekhar, M.P.V., et al., "Breast Stroma Plays a Dominant Regulatory Role in Breast Epithelial Growth and Differentiation: Implications for Tumor Development and Progression," *Cancer Research* 61:1320-1326 (2001).
Shiozawa, S., et al., "Identification of the Gene Loci that Predispose to Rheumatoid Arthritis," *International Immunology* 10(12):1891-1895 (1998).
Simpson, P.T., et al., "Molecular Evolution of Breast Cancer," *J Pathol* 205:248-254 (2005).
Slager, S.L., et al., "Confirmation of Linkage of Prostate Cancer Aggressiveness with Chromosome 19q," *Am. J. Hum. Genet.* 72:759-762 (2003).
Slaughter, D.P., et al., "'Field Cancerization' in Oral Stratified Squamous Epithelium Clinical Implications of Multicentric Origin," *Cancer* 6:963-8 (1953).
Smith, P. D., et al., "Novel p53 Mutants Selected in BRCA-Associated Tumours Which Dissociate Transformation Suppression from Other Wild-type p53 Functions," *Oncogene*, 18:2451-2459 (1999).
Taniguchi, T., et al., "S-Phase-Specific Interaction of the Fanconi Anemia Protein, FANCD2, with BRCA1 and RAD51," *Blood* 100(7):2414-2420 (2002).
Tran, Y., et al., "Novel Regions of Allelic Deletion on Chromosome 18p in Tumors of the Lung, Brain and Breast," *Oncogene* 17:3499-3505 (1998).
Tuhkanen, H., et al., "Genetic Alterations in the Peritumoral Stromal Cells of Malignant and Borderline Epithelial Ovarian Tumors as Indicated by Allelic Imbalance on Chromosome 3P," *Int. J Cancer* 109:247-252 (2004).
Umbricht, C.B., et al., "Human Telomerase Reverse Transcriptase Gene Expression and the Surgical Management of Suspicious Thyroid Tumors," *Clinical Cancer Research* 10:5762-5768 (2004).
Van Oijen, M.G.C.T., et al., "Oral Field Characterization: Carcinogen-induced Independent Events or Micrometastatic Deposits," *Cancer Epidemiology, Biomarkers & Prevention* 9:249-256 (2000).
Volinia, S., et al., "A MicroRNA Expression Signature of Human Solid Tumors Defines Cancer Gene Targets," *Proceedings of the National Academy of Sciences USA* 103(7):2257-2261 (2006).
Wang, X., et al., "p63 Expression in Normal, Hyperplastic and Malignant Breast Tissues," *Breast Cancer*, 9(3):216-219 (Jul. 2002).
Weber, F., et al., "A Limited Set of Human MicroRNA is Deregulated in Follicular Thyroid Carcinoma," *Journal Clinical Endocrinology & Metabolism* 91(9):3584-3591 (2006).

Weber, F., et al., "Gene-expression Profiling in Differentiated Thyroid Cancer—a Viable Strategy for the Practice of Genomic Medicine," *Future Oncol.* 1(4):497-510 (2005).
Weber, F., et al., "Silencing of the Maternally Imprinted Tumor Suppressor ARH1 Contributes to Follicular Thyroid Carcinogenesis," *The Journal of Clinical Endocrinology & Metabolism* 90(2):1149-1155 (2005).
Weber, F., et al., "Total-Genome Analysis of BRCA1/2-Related Invasive Carcinomas of the Breast Identifies Tumor Stroma as Potential Landscaper for Neoplastic Initiation," *The American Journal of Human Genetics* 78:961-972 (2006).
Weber, F., et al., "Variability in Organ-Specific *EGFR* Mutational Spectra in Tumour Epithelium and Stroma may be the Biological Basis for Differential Responses to Tyrosine Kinase Inhibitors," *British Journal of Cancer* 92:1922-1926 (2005).
Weber, F., M.D., et al., "Microenvironmental Genomic Alterations and Clinicopathological Behavior in Head and Neck Squamous Cell Carcinoma," *JAMA* 297(2)187-195 (2007).
Weigelt, B., et al., "No Common Denominator for Breast Cancer Lymph Node Metastasis," *British Journal of Cancer* 93:924-932 (2005).
Weiler, J., et al., "Anti-miRNA Oligonucleotides (AMOs): Ammunition to Target miRNAs Implicated in Human Disease?," *Gene Therapy* 13:496-502 (2006).
Wernert, N., et al., "Presence of Genetic Alterations in Microdissected Stroma of Human Colon and Breast Cancers," *Anticancer Research* 21:2259-2264 (2001).
Williams, H.K., et al., "Molecular Pathogenesis of Oral Squamous Carcinoma," *J. Clin Pathol: Mol Pathol* 53:165-172 (2000).
Witte, J.S., et al., "Genomewide Scan for Prostate Cancer—Aggressiveness Loci," *Am. J. Hum. Genet* 67:92-99 (2000).
Worsham, M.J., et al., "Fine-Mapping Loss of Gene Architecture at the CDKN2B ($p15^{INK4b}$), CDKN2A ($p14^{ARF}$, $p16^{INK4a}$), and *MTAP* Genes in Head and Neck Squamous Cell Carcinoma," *Arch Otolaryngol Head Neck Surg.* 132:409-415 (2006).
Yanaihara, N., et al., "Unique MicroRNA Molecular Profiles in Lung Cancer Diagnosis and Prognosis," *Cancer Cell* 9(3):189-198 (2006).
Yang, W.-W., et al.. "E2F6 Negatively Regulates Ultraviolet-Induced Apoptosis via Modulation of BRCA1," *Cell Death and Differentiation*, 14:807-817 (2007).
Yao, T.-P., et al., "Gene Dosage-Dependent Embryonic Development and Proliferation Defects in Mice Lacking the Transcriptional Integrator p300," *Cell* 93:361-372 (1998).
Yeh, M.W., et al., "False-Negative Fine-Needle Aspiration Cytology Results Delay Treatment and Adversely Affect Outcome in Patients with Thyroid Carcinoma," *Thyroid* 14(3):207-215 (2004).
Zeng, Y., et al., "MicroRNAs and Small Interfering RNAs can Inhibit mRNA Expression by Similar Mechanisms," *PNAS* 100(17):9779-9784 (2003).
SHDH Gene-GeneCards/DHSD Protein/DHSD Antibody; Succinate Dehydrogenase Complsex, Subunit D, Integral Membrane Protein; URL: http://www.genecards.org/cgi-bin/carddisp.pl?gene=SDHS&snp=75&rf=/home/genecards/current/website/carddisp.pl#snp>; downloaded Oct. 3, 2011.
Bayley, J.P., "Succinate Dehydrogenase Gene Variants and Their Role in Cowden Syndrome," *The American Journal of Human Genetics*, 88: 674-675 (2011).
Halushka, M.K., et al., "Patterns of Single-Nucleotide Polymorphisms in Candidate Genes for Blood-Pressure Homeostasis," *Nature Genetics*, 22: 239-247 (1999).
Hirschhorn, J.N., et al., "A Comprehensive Review of Genetic Association Studies," *Genetics in Medicine* 4(2): 45-61 (2002).
Lucentini, J., "Gene Association Studies Typically Wrong," *The Scientist*, 18: 20 (2004).
Ni, Y. and Eng, C., "Response to Bayley: Functional Study Informs Bioinformatic Analysis," *The American Journal of Human Genetics*, 88: 674-676 (2011).
Wacholder, S., et al., "Assessing the Probability That a Positive Report is False: An Approach for Molecular Epidemiology Studies," *J. Natl. Cancer Institute* 96(6): 434-442 (2004).

(56) References Cited

OTHER PUBLICATIONS

Pepe, M. S., et al., "Limitations of the Odds Ratio in Gauging the Performance of a Diagnostic, Prognostic, or Screening Marker," *American Journal of Epidemiology*, 159: 882-890 (2004).
Assié, G., et al., "Frequency of Germline Genomic Homozygosity Associated With Cancer Cases", *JAMA*, 299(12): 1437-1445 (2008).
Baysay, B.E., et al., "Repositioning the Hereditary Paraganglioma Critical Region on Chromosome Band 11q23", Hum. Genet., 104: 219-225 (1999).
*Restriction Requirement in regards to U.S. Appl. No. 12/462,053; dated Feb. 24, 2011.
*Restriction Requirement in regards to U.S. Appl. No. 12/633,539; dated Mar. 3, 2011.
*Restriction Requirement in regards to U.S. Appl. No. 12/343,871; dated Mar. 17, 2011.
*Reply to Restriction Requirement in regards to U.S. Appl. No. 12/343,871; dated May 5, 2011.
*Office Action in regards to U.S. Appl. No. 12/343,871; dated Jun. 9, 2011.
*Reply to Restriction Requirement in regards to U.S. Appl. No. 12/462,053; dated Aug. 24, 2011.
*Reply to Restriction Requirement in regards to U.S. Appl. No. 12/633,539; dated Sep. 1, 2011.
*Office Action in regards to U.S. Appl. No. 12/462,053; dated Oct. 18, 2011.
*Office Action in regards to U.S. Appl. No. 12/633,539; ; "Targets for Use in Diagnosis, Prognosis and Therapy of Breast Cancer," dated Oct. 28, 2011.
*Amendment/Response to Office Action in regards to U.S. Appl. No. 12/633,539; "Targets for Use in Diagnosis, Prognosis and Therapy of Breast Cancer," Date of Filing Jan. 26, 2012.
*Notice of Allowance in regards to U.S. Appl. No. 12/343,871; dated Dec. 16, 2011.
Notterman, D.A., et al., "Tumor Biology and Microarray Analysis of Solid Tumors: Colorectal Cancer as a Model System." In *Microarrays and Cancer Research*, Warrington, et al., eds., (MA: Eaton Publishing), Chapter 6, pp. 81-111 (2002).
Strausberg, R.L. and Klausner, R.D., "Reading the Molecular Signatures of Cancer.", In *Microarrays and Cancer Research*, Warrington, et al., eds, (MA: Eaton Publishing), pp. xi-xvi (2002).
*Notice of Allowance for U.S. Appl. No. 12/633,539, "Targets for Use in Diagnosis, Prognosis and Therapy of Breast Cancer", dated Feb. 22, 2012.
*Office Action for U.S. Appl. No. 12/727,039, "Targets for Use in Diagnosis, Prognosis and Therapy of Cancer", dated Jan. 11, 2013.
*Reply to Office Action for U.S. Appl. No. 12/727,039, "Targets for Use in Diagnosis, Prognosis and Therapy of Cancer", filed Jul. 11, 2013.
*Final Office Action for U.S. Appl. No. 12/727,039, "Targets for Use in Diagnosis, Prognosis and Therapy of Cancer", dated Aug. 26, 2013.
*Request for Continued Examination for Action for U.S. Appl. No. 12/727,039, "Targets for Use in Diagnosis, Prognosis and Therapy of Cancer", filed Feb. 26, 2014.
*Notice of Allowance for U.S. Appl. No. 13/418,310, "Method of Detecting Follicular Thyroid Carcinoma" dated Jan. 29, 2014.
Rosenberg, N.A., et al., "Genetic Structure of Human Populations," *Science*, 298: 2381-2385 (2002).
Rosenberg, N.A., et al., "Supplementary information for 'Genetic structure of human populations,'" 12 pages (2002).
*Office Action in regards to U.S. Appl. No. 13/445,688, "Methods and Compositions for Detection of Cowden Syndrome (CS)", dated May 22, 2015.
Montani, et al., "No Mutations but an Increased Frequency of SDHx Polymorphisms in Patients with Sporadic and Familial Medullary Thyroid Carcinoma," *Endocrine-Related Cancer*, 12:1011-1016 (2005).
*Office Action in regards to U.S. Appl. No. 13/445,688, "Methods and Compositions for Detection of Cowden Syndrome (CS)", dated Dec. 23, 2013.
*Office Action in regards to U.S. Appl. No. 13/445,688, "Methods and Compositions for Detection of Cowden Syndrome (CS)", dated Apr. 15, 2013.
GeneCard for the SDHB gene, available via url: <genecards.org/cgi-bin/carddisp.pl?gene=SDHB>, printed on Apr. 8, 2013.
GeneCard for the SDHD gene, available via url: <genecards.org/cgi-bin/carddisp.pl?gene=SDHB>, printed on Apr. 8, 2013.
Bayley, J.P., "Ths SDH Mutation Database: An Online Resource for Succinate Dehydrogenase Seqence Variants Involved in Pheopchromocytoma, Paraganglioma and Mitochondrial Complex II Deficiency," *BMC Medical Genetics*, 6(39): pp. 1-6, (2005).
Cascon, A., et al., "Genetic and Epigenetic Profile of Sporadic Pheochromocytomas" *J. Med. Genet*, 41: pp. 1-5 (2004).
*Restriction Requirement in regards to U.S. Appl. No. 13/445,688, "Methods and Compositions for Detection of Cowden Syndrome (CS) and CS-Like Syndrome", dated Nov. 15, 2012.
*Reply to Restriction Requirement in regards to U.S. Appl. No. 13/445,688, "Methods and Compositions for Detection of Cowden Syndrome (CS) and CS-Like Syndrome," date of filing: Feb. 22, 2013.
International Search Report, issued in International Application No. PCT/US2007/015265, entitled "Targets for Use in Diagnosis, Prognosis and Therapy of Cancer," dated Jul. 2, 2008 (24 pages).
International Preliminary Report on Patentability, issued in International Application No. PCT/US2007/015265, entitled "Targets for Use in Diagnosis, Prognosis and Therapy of Cancer," dated Jan. 15, 2009 (13 pages).
*Restriction Requirement in regards to U.S. Appl. No. 13/418,310, "Targets for Use in Diagnosis, Prognosis and Therapy of Cancer," dated Sep. 25, 2012.
*Reply to Restriction Requirement in regards to U.S. Appl. No. 13/418,310, "Targets for Use in Diagnosis, Prognosis and Therapy of Cancer," date of filing: Oct. 25, 2012.
*Office Action in regards to U.S. Appl. No. 13/418,310, "Targets for Use in Diagnosis, Prognosis and Therapy of Cancer," dated May 21, 2013.
*Amendment/Response to Office Action in regards to U.S. Appl. No. 13/418,310, "Targets for Use in Diagnosis, Prognosis and Therapy of Cancer," date of filing: Nov. 21, 2013.
Restriction Requirement in regards to U.S. Appl. No. 12/727,039, Targets for Use in Diagnosis, Prognosis and Therapy of Cancer, dated May 30, 2012.
*Reply to Restriction Requirement in regards to U.S. Appl. No. 12/727,039, Targets for Use in Diagnosis, Prognosis and Therapy of Cancer, date of filing: Oct. 1, 2012.
*Office Action in regards to U.S. Appl. No. 12/727,039, Targets for Use in Diagnosis, Prognosis and Therapy of Cancer, dated Jan. 15, 2015.

FIG. 1

MnSOD Expression

FIG. 2A

Control

SDHD: His50Arg

Positive control: control + THBP

FIG. 2C

SDHB: GCG3GGG (Ala3Gly)

CAAG AT GG CG GGG GT C C T C G  (SEQ ID NO.: 1)
         170       180

SDHD: GGT12AGT (Gly12Ser)

3 C C G T T T G C G G T G C C C T A C  (SEQ ID NO.: 2)
          160           170

SDHD: CAC50CGC (His50Arg)

3 C A C A T A CA C T T G T C A C C  (SEQ ID NO.: 3)
                  150

SDHD: CAC145AAC (His145Asn)

T T T CAA C T AT CA C G AT GT G G G C  (SEQ ID NO.: 4)
      100              110              120

SEQUENCE LISTING

```
<160> NUMBER OF SEQ ID NOS: 4

<210> SEQ ID NO 1
<211> LENGTH: 20
<212> TYPE: DNA
<213> ORGANISM: Unknown
<220> FEATURE:
<223> OTHER INFORMATION: sequence of germline heterozygous mutation of
      SDH gene identified in patients with CS/CS-like
      phenotypes

<400> SEQUENCE: 1
caagatggcg ggggtcctcg                                              20

<210> SEQ ID NO 2
<211> LENGTH: 18
<212> TYPE: DNA
<213> ORGANISM: Unknown
<220> FEATURE:
<223> OTHER INFORMATION: sequence of germline heterozygous mutation of
      SDH gene identified in patients with CS/CS-like
      phenotypes

<400> SEQUENCE: 2
ccgtttgcgg tgccctac                                                18

<210> SEQ ID NO 3
<211> LENGTH: 17
<212> TYPE: DNA
<213> ORGANISM: Unknown
<220> FEATURE:
<223> OTHER INFORMATION: sequence of germline heterozygous mutation of
      SDH gene identified in patients with CS/CS-like
```

```
        phenotypes

<400> SEQUENCE: 3
cacatacact tgtcacc                                                    17

<210> SEQ ID NO 4
<211> LENGTH: 22
<212> TYPE: DNA
<213> ORGANISM: Unknown
<220> FEATURE:
<223> OTHER INFORMATION: sequence of germline heterozygous mutation of
      SDH gene identified in patients with CS/CS-like
      phenotypes

<400> SEQUENCE: 4
tttcaactat cacgatgtgg gc                                              22
```

METHODS AND COMPOSITIONS FOR DETECTION OF COWDEN SYNDROME (CS) AND CS-LIKE SYNDROME

RELATED APPLICATION

This application is a continuation of U.S. application Ser. No. 13/445,688 filed on Apr. 12, 2012 which is a continuation of U.S. application Ser. No. 12/462,053 filed on Jul. 27, 2009, which claims the benefit of U.S. Provisional Application No. 61/137,042, filed on Jul. 25, 2008. The entire teachings of the above applications are incorporated herein by reference.

GOVERNMENT SUPPORT

The invention was supported, in whole or in part, by a grant 1P01CA124570-01A1 from the National Cancer Institute. The Government has certain rights in the invention.

INCORPORATION BY REFERENCE OF MATERIAL IN ASCII TEXT FILE

This application incorporates by reference the Sequence Listing contained in the following ASCII text file:
a) File name: 37861044003SEQLIST.txt; created Mar. 8, 2016, 1.46 KB in size.

BACKGROUND OF THE INVENTION

Phosphatase and tensin homolog deleted on chromosome ten (PTEN [MIM 601728]) is a ubiquitous tumor suppressor that plays a role in both heritable and sporadic neoplasias (Zbuk, K. M., et al. *Nat. Rev. Cancer,* 7:35-45 (2007)). Cowden syndrome (CS [MIM 158350]) is a difficult to recognize, autosomal dominant inherited cancer syndrome characterized by benign and malignant breast, thyroid and endometrial neoplasias in addition to cutaneous findings and macrocephaly (Eng, C., *Hum. Mut.,* 22:183-198 (2003)). Germline PTEN mutations have been found in 85% of those with classic CS while 15% remain mutation negative despite extensive analyses including the promoter and looking for large deletions and rearrangements (Marsh, D. J., et al., *Hum. Mol. Genet.,* 7:507-515 (1998); Zhou, X. P., et al., *Am. J. Hum. Genet.,* 73:404-411 (2003)). Many more patients with features reminiscent of CS, not meeting diagnostic criteria (National Comprehensive Cancer Center Practice Guidelines (NCC); Table 1) and referred to as CS-like, are evaluated by clinicians for CS and cancer-risk. CS is believed to be without genetic heterogeneity (Nelen, M. R., et al., *Nat. Genet.,* 13:114-116 (1996)) to date, only PTEN has been implicated in this syndrome. However, there likely exist other susceptibility genes for CS and CS-like phenotypes, especially in the latter, which appear to be a heterogeneous disease.

Therefore, a better understanding of CS syndrome and CS-like syndrome is needed in order to provide better detection methods for these syndromes.

SUMMARY OF THE INVENTION

In one aspect, the invention is directed to a method of detecting Cowden syndrome (CS) or CS-like syndrome in an individual comprising detecting the presence of a mutated succinate dehydrogenase B (SDHB), mutated succinate dehydrogenase D (SDHD) or combination thereof in the individual, wherein detection of a mutated SDHB, SDHD or a combination thereof indicates that the individual is positive for CS or CS-like syndrome.

In another aspect, the invention is directed to a method of determining whether an individual is at risk for developing Cowden syndrome (CS) or CS-like syndrome comprising detecting the presence of a mutated succinate dehydrogenase B (SDHB), mutated succinate dehydrogenase D (SDHD) or combination thereof in the individual, wherein detection of a mutated SDHB, SDHD or a combination thereof indicates that the individual is at risk for developing for CS or CS-like syndrome.

In yet another aspect, the invention is directed to an article of manufacture for detecting Cowden syndrome (CS) or Cowden-like syndrome in an individual, comprising one or more agents that detects mutated succinate dehydrogenase B (SDHB), mutated succinate dehydrogenase D (SDHD) or combination thereof in the individual, and instructions for use.

BRIEF DESCRIPTION OF THE DRAWINGS

FIG. 1 is a schematic of the experimental design for SDH mutation testing and functional analysis. Note PTEN gene test encompasses intragenic PCR-based mutation analysis, promoter and large deletion analysis. From the 2,270 PTEN mutation negative CS/CS-like individuals, the most proximal (i.e., most recent) consecutive 375 PTEN mutation negative subjects were selected to proceed to MnSOD expression analysis. It is these 375 subjects that represent the series for this SDH study.

FIGS. 2A-2E show genetic and biochemical analyses of CS/CS-like patients without germline PTEN mutations reveal a subset with germline SDH mutations resulting in biochemical dysfunction.

FIG. 3 shows a proposed Model for the Final Common Pathway of Putative Mitochondrial Dysfunction Resulting from Either PTEN or SDHx Mutation in Cowden and Cowden-like Syndromes. A simplified version of the signaling pathways involved in tumorigenesis in the setting of dysfunctional PTEN or SDH (represented by hatched colors). These pathways cross-talk leading to the final common outcome of tumor angiogenesis, cell proliferation. and inhibition of apoptosis. Note that one of the functions of SDH is the conversion of succinate to fumarate as part of the Kreb's tricarboxylic acid cycle. SDH dysfunction will therefore lead to an accumulation of succinate, which inhibits prolyl hydroxylases (PHD) and subsequently leads to the stabilization of HIF-la. The stabilization of the latter also occurs a number of steps downstream of dysfunctional PTEN signaling. It is interesting to note that activated Akt (P-Akt) can increase ATP levels which result in increased ROS, presumably via mitochondrial dysfunctional signaling. This is postulated to set up a double feedback loop linking both the PTEN and SDH pathways.

DETAILED DESCRIPTION OF THE INVENTION

Clues to disease etiology are often obtained by examining whether certain CS/CS-like clinical features resemble those in other syndromes, by examining downstream signaling, and/or by looking at phenotype in murine models. In this situation, the murine model only vaguely resembles human CS (Zbuk, K. M., et al. *Nat. Rev. Cancer,* 7:35-45 (2007)). One prominent feature in the mouse model is pheochromocytoma, a neoplasia of the adrenal medulla, and its closely related neural crest-derived paraganglioma (PGL) (Satmbolic, V., et al., *Cancer Res.,* 60:3605-3611 (2000). Pheochromocytoma and PGL are not known component features of CS (NCCN; Table 1).

Succinate debydrogenase (SDH) belongs to mitochondrial complex II, which participates in both the electron transport chain and the Kreb's cycle (reviewed by Eng, C., et al., *Nat. Rev. Cancer,* 3:193-202 (2003)). SDH comprises four subunits, SDHA, B, C and D, each of which is encoded by autosomal genes on 3 different chromosomes. While homozygous/compound heterozygous mutations in SDHA (MIN 600857) cause severe neurological dysfunction and cardiomyopathy, heterozygous germline mutations in SDHB-D (MIM 185470, 602413, 602690) cause a pheochromocytoma-PGL syndrome (Neumann, H. P. H., et al., *N. Engl. J. med.,* 346:1459-1466 (2002)). Approximately 1%-5% of carriers of SDHB or SDHD mutations have been found to have renal cell carcinoma or papillary thyroid cancer (Vanharanta, S., et al., *Am. J. Hum. Genet.,* 74:153-159 (2004); Benn, D. E., et al., *J. Clin. Endocrinol. Metab.,* 91:827-836 (2006)) which are also features of CS. Fumarate hydratase (FH) is the enzyme immediately downstream of SDH. Homozygous germline mutations cause severe neurological dysfunction and death while heterozygous mutations are associated with hereditary leiomyomatosis and renal cell carcinoma (HLRCC) (Launonen, V., et al., *Proc. natl. Acad. Sci., USA,* 98:3387-3392 (2001)). In vitro evidence also suggests that mitochondrial caspases and HIF1 are downstream molecules of the PTEN pathway (Zundel, W., et al., *Genes Develop.,* 14:391-396 (2000); Tang, Y., et al., *Cancer Res.,* 66:736-742 (2006)). The invention described herein is based, in part, on the discovery that SDHx represent susceptibility genes, other than PTEN, for CS/CS-like syndromes.

Individuals with PTEN mutations have Cowden syndrome (CS), associated with breast, thyroid and endometrial neoplasias. Many more patients with features of CS, not meeting diagnostic criteria (termed CS-like), are evaluated by clinicians for CS-related cancer-risk. Germline mutations in succinate dehydrogenase subunits SDHB-D cause pheochromocytoma-paraganglioma syndrome. One to five percent SDHB/SDHD mutation carriers have renal cell or papillary thyroid carcinomas, which are also CS-related features. As described herein, SDHB-D are susceptibility genes for some PTEN mutation negative individuals with CS-like cancers.

Specifically, germline SDHB-D mutation analysis in 375 PTEN mutation negative CS/CS-like individuals was performed followed by functional analysis of identified SDH mutations/variants. Of 375 PTEN mutation negative CS/CS-like individuals, 74 (20%) had increased manganese superoxide dismutase (MnSOD) expression, a manifestation of mitochondrial dysfunction. Amongst these, 10 (13.5%) had germline mutations/variants in SDHB (N=3) or SDHD (7), not found in 700 controls (P<0.001). Compared to PTEN mutation positive CS/CS-like individuals, those with SDH mutations/variants were enriched for carcinomas of the female breast (6/9 SDH vs, 30/107 PTEN, p<0.001), thyroid (5/10 vs. 15/106, <0.001) and kidney (2/10 vs. 4/230, p=0.026). In the absence of PTEN alteration, CS/CS-like-related SDH mutations/variants showed increased phosphorylation of AKT and/or MAPK, downstream manifestations of PTEN dysfunction. Germline SDH mutations/variants occur in a subset of PTEN mutation-negative CS/CS-like individuals and are associated with increased frequencies of breast, thyroid and renal cancers beyond those conferred by germline PTEN mutations. Thus, SDH testing can be used for germline PTEN mutation-negative CS/CS-like individuals, especially in the setting of breast, thyroid and/or renal cancers.

Accordingly, in one aspect, the invention is directed to a method of detecting (diagnosing) Cowden syndrome (CS) or CS-like syndrome in an individual comprising detecting the presence of a mutated succinate dehydrogenase B (SDHB), mutated succinate dehydrogenase D (SDHD) or combination thereof in the individual, wherein detection of a mutated SDHB, SDHD or a combination thereof indicates that the individual is positive for CS or CS-like syndrome (indicates a diagnosis of CS or CS-like syndrome in the individual).

In another aspect, the invention is directed to a method of determining whether an individual is at risk for developing Cowden syndrome (CS) or CS-like syndrome comprising detecting the presence of a mutated succinate dehydrogenase B (SDHB), mutated succinate dehydrogenase D (SDHD) or combination thereof in the individual, wherein detection of a mutated SDHB, SDHD or a combination thereof indicates that the individual is at risk for developing for CS or CS-like syndrome.

As used herein, a "mutated SDHB" or a "mutated SDHD" is a SDHB or SDHD that has a sequence (e.g., nucleic acid (e.g., DNA, such as genomic DNA; RNA) sequence, amino acid sequence) that differs from, or is a variant of, the normal or wild type SDHB sequence or SDHD sequence. In one aspect of the invention, the mutated SDHB has a nucleic acid sequence that encodes an amino acid sequence comprising an Ala3Gly mutation, a Ser163Pro mutation or a combination thereof. In another aspect of the invention, the mutated SDHD has a nucleic acid sequence that encodes an amino acid sequence comprising a Gly12Ser mutation, a His50Arg mutation, a His145Asn mutation or a combination thereof.

The methods can further comprise obtaining a sample from the individual. A suitable sample for use in the methods of the invention is any sample obtained from the individual that comprises the individual's SDHB or SDHD. Examples of suitable samples include a tissue sample (e.g., organ, placenta), a cell sample (e.g., peripheral leukocytes; cell lysate), a fluid sample (e.g., blood, amniotic fluid, cerebrospinal fluid, urine, lymph) and any combination thereof. Methods of obtaining such samples and/or extracting SDHB and/or SDHD nucleic acid or protein from such samples are described herein and known to those of skill in the art.

As will be apparent to one of skill in the art, a variety of methods can be used to determine the presence of a mutated succinate dehydrogenase B (SDHB), a mutated succinate dehydrogenase D (SDHD) or combination thereof in the individual or in a sample obtained from the individual.

In one aspect, the sequence of the SDHB, SDHD or combination thereof, in the individual is determined. A variety of methods for determining the nucleic acid and/or amino acid sequence of SDHB and/or SDHD can be used. For example, the amino acid sequence of the SDHB, SDHD or combination thereof is determined using polymerase chain reaction (PCR) amplification and direct sequencing (McWhinney, S. R., et al., *J. Clin. Endocrinol. Metab.*, 89:5694-5699 (2004); Mutter, G. L., et al., *J. Natl. Cancer Inst.*, 92:924-930 (2000)).

In addition or alternatively, the function of the SDHB, SDHD or combination thereof, in the individual is determined. There are also a variety of methods that can be used to determine the function of SDHB and/or SDHD. For example, in one aspect, the function of the SDHB, SDHD or combination thereof is determined by measuring the production of reactive oxygen species (ROS) wherein an increase in the production of ROS indicates the presence of a mutated SDHB, SDHD or a combination thereof. The increase in ROS production is at least about a 1-fold increase compared to a control. In another aspect, the increase in ROS production is at least about a 1.5-fold increase compared to a control. The production of ROS can be measured using, for example, using carboxy-H2DCFDA and confocal microscopy.

In another aspect, the function of SDHB, SDHD or a combination thereof is determined by detecting activation of an antiapoptotic/proproliferative AKT (protein kinase B) pathway, a mitogen-activated kinase (MAPK) pathway or a combination thereof. Activation of these pathways can be determined by detecting the presence of phosphorylated AKT, phosphorylated MAPK or a combination thereof, using, for example, one or more antibodies having binding specificity for the phosphorylated AKT or the phosphorylated MAPK.

The methods of the invention can further comprise comparing the presence of a mutated SDHB, SDHD or combination thereof in the individual to a control. Suitable controls for use in the methods provided herein are apparent to those of skill in the art. For example, a suitable control can be established by assaying the SDHB and/or SDHD sequence and/or function of one or more (e.g., a large sample of) individuals which do not have CS or CS-like syndrome. Alternatively, a control can be obtained using a statistical model to obtain a control value (standard value; known standard). See, for example, models described in Knapp, R. G. and Miller M. C. (1992) Clinical Epidemiology and Biostatistics, William and Wilkins, Harual Publishing Co. Malvern, Pa., which is incorporated herein by reference.

As used herein the term "individual" includes animals such as mammals, as well as other animals, vertebrate and invertebrate (e.g., birds, fish, reptiles, insects (e.g., *Drosophila* species), mollusks (e.g., *Aplysia*). Preferably, the animal is a mammal. The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include primates (e.g., humans, monkeys, chimpanzees), rodents (e.g., rats, mice, guinea pigs) and ruminents (e.g., cows, pigs, horses).

In one aspect of the invention, the individual is negative for a mutated phosphatase and tensin homolog deleted on chromsome ten (PTEN). In another aspect of the invention, the individual has elevated expression levels of maganese superoxide dismutase. In yet another aspect of the invention, the individual has a carcinoma of the breast, thyroid (e.g., papillary thyroid carcinoma), kidney (e.g., renal cell carcinoma) or a combination thereof.

The methods of detection of CS and/or CS-like syndrome can be used in combination with other methods used to detect CS and/or CS-like syndrome (e.g., operational diagnostic criteria of the International Cowden Consortium, Table 1).

The invention is also directed to an article of manufacture for detecting Cowden syndrome (CS) or Cowden-like syndrome in an individual, comprising one or more agents that detects mutated succinate dehydrogenase B (SDHB), mutated succinate dehydrogenase D (SDHD) or combination thereof in the individual, and instructions for use. In one aspect, the agent detects the sequence of the SDHB, SDHD or combination thereof. In another aspect, the agent detects the production of reactive oxygen species (ROS). In yet another aspect, the agent detects phosphorylated AKT, phosphorylated MAPK or a combination thereof using one or more antibodies having binding specificity for the phosphorylated AKT, the phosphorylated MAPK or a combination thereof.

EXEMPLIFICATION

Materials And Methods

Patients

Figure 1:
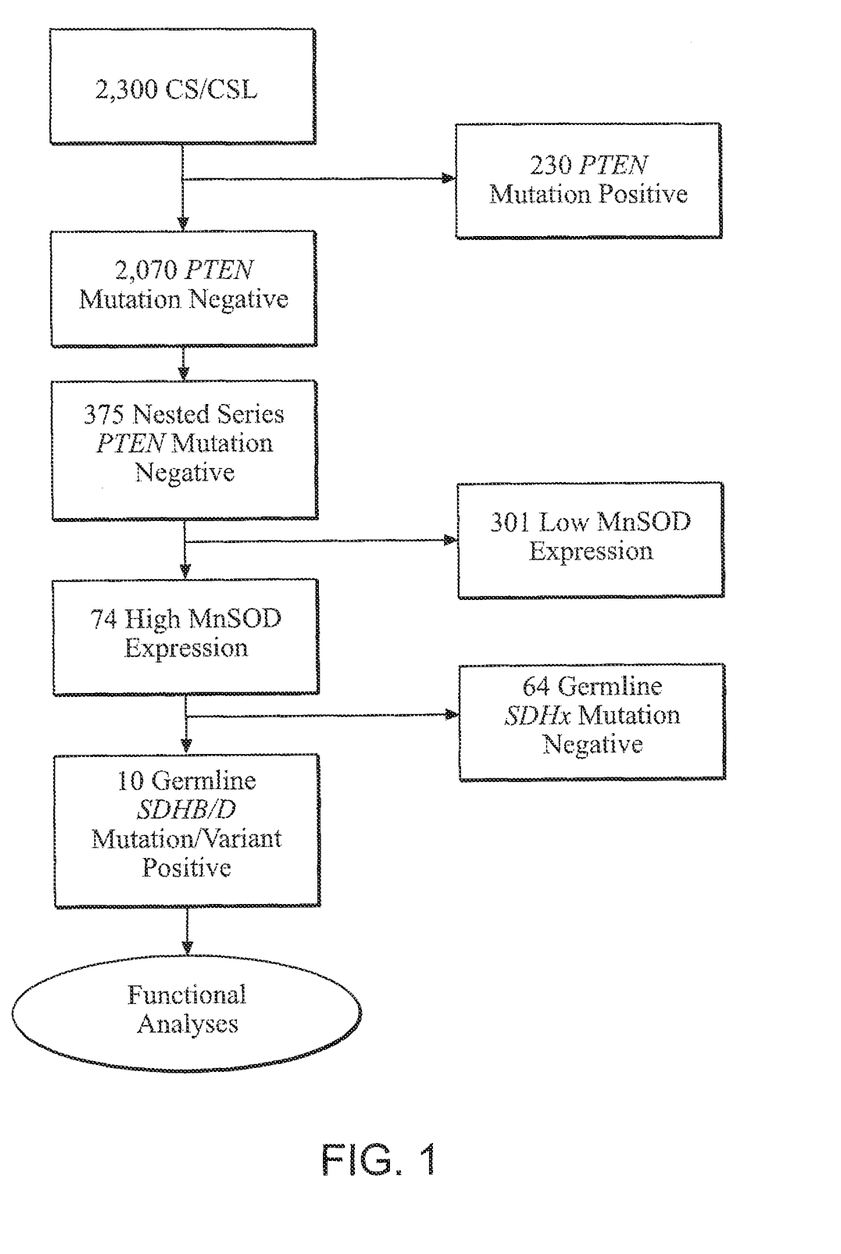

Peripheral blood samples accrued from 375 CS and CS-like individuals, who were germline PTEN mutation negative after comprehensive mutation analysis which includes all 9 coding exons, flanking intronic regions, and minimal promoter region of PTEN and examination for large deletions and rearrangements, were utilized (FIG. 1). Classic CS was diagnosed when the operational diagnostic criteria of the International Cowden Consortium were met (Table 1) (Liaw, D., et al., *Nat. Genet.*, 16:64-67 (1997)). The diagnosis of CS-like was made when an individual did not meet any of the strict diagnostic criteria but had features that were one or two criteria short of the operational diagnostic criteria (Table 1). Peripheral blood samples from 700 normal white populational controls of northern and western European origin, which were anonymized prior to storage and analysis were utilized. Informed consent was obtained for all subjects (CS/CS-like individuals and controls) in accordance with procedures and protocols approved by the respective Human Subjects Protection Committee of each participating institution. All subjects, whether CS/CS-like, or controls, participated on a voluntary basis. See Ni, Y., et al., *Am. J. Hum. Genet.*, *(AJHG)*, 83:261-268 (2008) which is incorporated herein by reference.

Mutation Analysis

Genomic DNA was extracted from peripheral leukocytes and PCR amplification and direct sequencing (ABI3730xI) of PTEN, SDHB, SDHC and SDHD were performed as previously reported (McWhinney, S. R., et al., *J. Clin. Endocrinol. Metab.*, 89:5694-5699 (2004); Mutter, G. L., et al., *J. Natl. Cancer Inst.*, 92:924-930 (2000), which are herein incorporated by reference). It is important to note that all 700 controls had the entire sequence of SDHB, SDHC and SDHD sequenced and no variants identified.

Cell Lines and Cell Culture

Human immortalized lymphoblast cell lines obtained from patients and controls were cultured in RPMI 1640 supplemented with 20% fetal bovine serum (FBS). All cell lines were cultured at 37° C. with 5% $CO_2$.

Protein Analysis

Whole-cell lystates were prepared using Mammalian Protein Extraction Reagent (Pierce, Rockford, Ill.) supplemented with protease inhibitor cocktail (Sigma). Lysates were either separated by SDS-PAGE and transferred to nitrocellulose or applied to nitrocellulose using a dotblot apparatus (BioRad). The resulting blots were then subjected to western blot analysis (Weng, L. P., et al., *Hum. Mol. Genet.*, 11:1687-1696 (2002)) for either: SDHB (AbCam, USA), MnSOD (Upstate Biotechnology, Waltham, Mass.), PTEN (Weng, L. P., et al., *Hum. Mol. Genet.*, 11:1687-1696 (2002)) (Cascade Biosciences, Portland, Oreg., USA) P-MAPK, MAPK, AKT, P-AKT or actin (Cell Signaling Co, Beverly, Mass., USA). For the phosphorylation of MAPK an antibody that recognizes the activation phosphorylation of residues Thr187 and Thr189 of the p44-MAPK and the equivalent phosphorylation in p42-MAPK was utilized. For Akt phosphorylation, an antibody that recognizes the activation phosphorylation of Ser473 was utilized. Both of these antibodies are traditionally utilized to monitor phosphorylation, and thus activation, of these enzymes. Proteins were detected using ECL substrate (Amersham Biosciences, Inc., Chicago, Ill., USA) and autoradiography.

Confocal Microscopy

Images were collected with a Leica TCS SP2 AOBS confocal microscope (Leica Micro-Systems, Heidelberg, GmbH) using a HCX Plan Apo 63x/1.4NA oil immersion lens. The cells were excited with 488 nm light from an Argon laser and emitted light was collected between 500-550 nm. Collection parameters remained constant for all samples. Quantitation of ROS was performed by standard FACS (HFE), with controls normalized to 1.

Statistical Analysis

The frequency of each of the established CS-specific component carcinomas (breast and epithelial thyroid) and 2 of the strongly suspected component carcinomas (renal cell and endometrial) in SDHx mutation positive individuals were compared to that in a cohort of 230 PTEN mutation positive individuals with CS/CS-like phenotypes. Both groups were ascertained by identical clinical criteria as noted in the first section of the Methods. Fisher's 2-tailed Exact Test was applied with significance at $p<0.05$.

Results

Figure 2A:
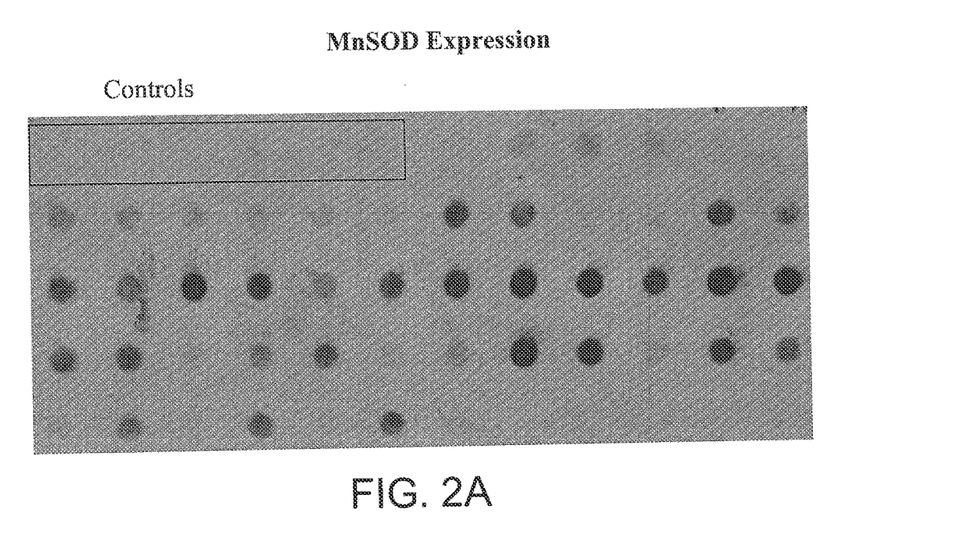
FIG. 2A shows dot blots to screen for increased MnSOD protein levels. Boxed dots represent controls with low MnSOD levels.
Figure 2B:
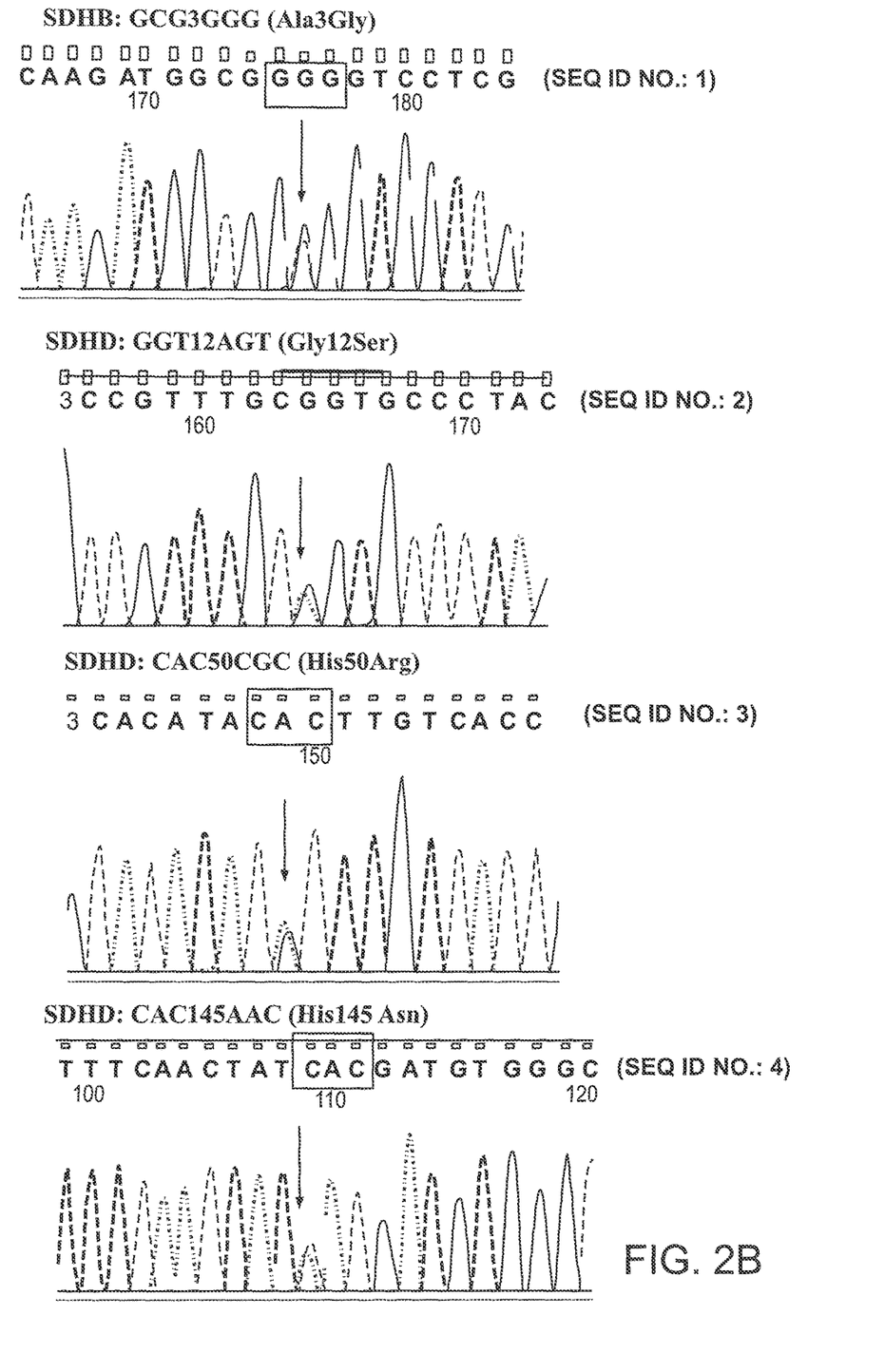
FIG. 2B shows illustrative sequencing chromatograms of germline heterozygous mutations of SDH genes identified in patients with CS/CS-like phenotypes (mutations as noted above each chromatogram). The germline mutations/variants are heterozygous manifested by overlapping peaks (arrows).

To address the hypothesis, protein lysates from 375 PTEN mutation negative CS/CS-like individuals were screened for increased expression of manganese superoxide dismutase (MnSOD) because the latter is a good indicator and first screen for general (complex I-VI, especially complex II or V) mitochondrial dysfunction (FIG. 1). Dot blot analysis of these patients' protein lysates and 18 population controls identified 74 (20%) PTEN mutation negative patients with elevated MnSOD protein levels (FIGS. 1 and 2A). These 74 were subjected to SDHx mutation analysis (FIG. 1). Those that did not have elevated MnSOD levels were not included because a pilot study of 40 CS/CS-like PTEN mutation negative levels without elevated MnSOD were shown not to harbor any SDHx mutations (Eng et al., unpublished data). Of the 74 with germline elevations of MnSOD, 10 (13.5%; 95% confidence intervals (CI) 7.3-23.3%) were found to have germline mutations/variants in SDHB (N=3) or SDHD (N=7): Ala3Gly and Ser163Pro (N=2) in SDHB and His145Asn (N=1), His50Arg (N=2) and Gly12Ser (N=4) in SDHD (FIG. 2, Table 2). None of these SDH mutations were found in 700 normal controls ($P<0.001$, Fisher's 2-tailed exact test). All 3 genes, SDHB/C/D, were sequenced in the controls and no variants uncovered.

Figure 2C:
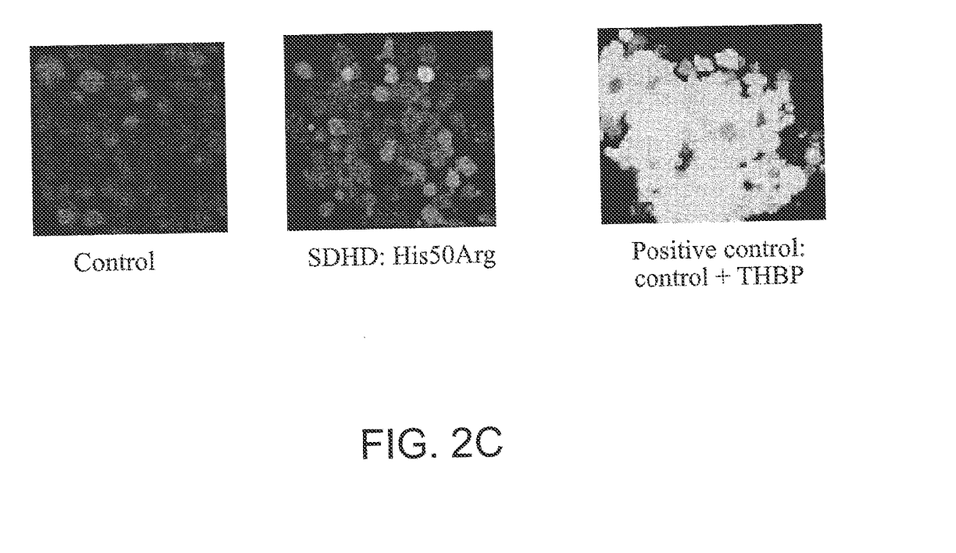
FIG. 2C shows increased ROS in peripheral lymphoblasts from an individual with germline SDHD His50Arg. Increased. ROS levels are measured by increased carboxy-H2DCFDA staining as seen in cultured lymphoblast cells from the patient with SDHD His50Arg mutation denoting 1.5-fold higher ROS levels (middle) compared to a lymphoblast cell line derived from a normal control individual (left; P<0.001, Student T-test, 3 replicates). Finally, a control lymphoblast cell line treated with tert-butyl hydroperoxide for 90 min was used as a super-positive control and supra-induced ROS expression is noted by markedly increased carboxy-H2DCFDA staining (right).

Then the 5 different SDH mutations/variants, identified in the 10 CS/CS-like individuals, were subjected to functional analysis (FIGS. 2A-2E and Table 3). First, the increased MnSOD protein levels noted on dot blot were confirmed by Western blot (Table 3). Because it is known that SDH dysfunction can result in increased production of reactive oxygen species (ROS) (Ishii, T., et al., *Cancer Res.*, 65:203-209 (2005); Slane, B. G., et al., *Cancer res.*, 66:7615-7620 (2006)), the pathogenicity of these different SDH mutations was also tested by direct measurements of increased ROS levels using (5-(and-6)-carboxy-2'7'-dichlorodihydrofluorescein diacetate (carboxy-H2DCFDA) and confocal microscopy (FIG. 2C, Table 3). SDHB Ser163Pro, SDHD Gly12Ser and His50Arg resulted in increased ROS levels (Table 3). SDHB Ala3Gly and SDHD His145Asn, in contrast, had normal ROS levels (Table 3).

Figure 2D:
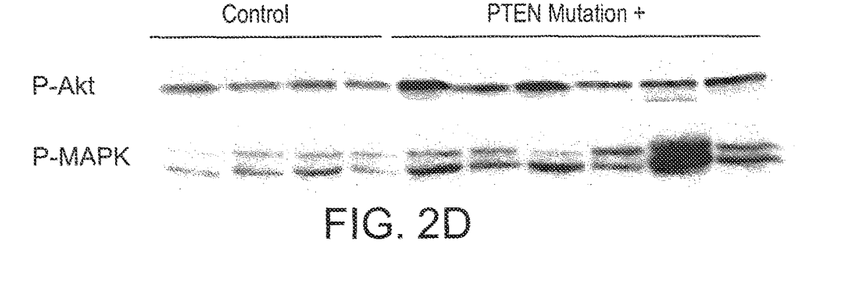
FIG. 2D shows protein expression of P-AKT and P-MAPK (P-ERK44/42) in germline heterozygous PTEN mutation positive individuals. Note different mutations result in varying activation of P-Akt and/or P-MAPK.

PTEN is a tumor suppressor which down-regulates the anti-apoptotic/pro-proliferative AKT (protein kinase B) (Stambolic, V., et al., *Cell*, 95:29-39 (1998)) and mitogen activated kinase (MAPK) pathways (Weng, L., et al., *Hum. Mol. Genet.*, 11:1687-1696 (2002)). Therefore, PTEN dysfunction is associated with activation of these pathways, whose downstream readouts include phosphorylated AKT (p-Akt) and MAPK (p-MAPK) (p42/44ERKs) (FIG. 2D). All 10 CS/CS-like patients with the germline SDHB/D mutations showed activation of AKT and MAPK manifested by increased phosphorylated AKT and MAPK in their germline, when compared to normal controls (FIG. 2D). Interestingly, the SDHD His145Asn mutation and the SDHB Ala3Gly mutation, which did not affect ROS, showed activation of the MAPK pathway and no or only mild activation of the AKT pathway (Table 3, FIG. 2E).

Renal cell carcinoma was present in 2/10 (20%; 95% CI 5-52%) CS/CS-like individuals with germline SDH mutations/variants (Table 2) compared to 4/230 (1.2%; 95% CI 0.5-4.5%) with germline PTEN mutations ($p=0.03$, Fisher's 2-tailed exact test). Epithelial thyroid carcinoma was found in 5 of 10 (50%; 95% CI 25-76%) SDH mutation positive individuals (Table 2) compared to 15/206 (7.2%; 95% CI 4-12%) with germline PTEN mutations ($p<0.001$). Interestingly, the histology of all the SDH-related thyroid cancers was papillary thyroid carcinoma compared to only one of the 15 thyroid cancers in PTEN mutation carriers ($P<0.001$). Female breast cancer was found in 6 of 9 (66.7%; 95% CI 36-88%) SDHx mutation positive women (Table 2) compared to 28% (95% CI 22-34%) of women with germline PTEN mutations ($p<0.001$). It is important to note that the frequencies of uterine endometrial carcinomas and uterine leiomyomas in our women with SDHx mutations were similar to those in women with PTEN mutations ($P>0.05$).

One individual, the 55-year old man with germline SDHD His50Arg was incidentally found to have a unilateral pheochromocytoma.

Discussion

The observations described herein indicate that a subset of CS or CS-like individuals, without germline PTEN mutations, may be accounted for by germline mutations or variants in either the SDHB SDHD, but not SDHC, genes. SDHB and SDHD are the susceptibility genes for familial pheochromocytoma-PGL syndrome (Eng, C., et al., *Nature Rev. Cancer*, 3:193-202 (2003)). At least one of the 5 different mutations found in the 10 CS/CS-like individuals, SDHD His145Asn, has never been described before in individuals and families with pheochromocytoma and/or PGL (SDHx Mutation Database). Because these mutations are neither in dbSNP nor in our 700 control individuals, this almost certainly is a pathogenic germline mutation. His145 is also highly conserved through mouse, sheep and cow, arguing for the biological importance of this amino acid residue. Functional analyses corroborate the pathogenicity of this missense mutation. This mutation shows activation of the MAPK, but not AKT, pathway (Table 3, FIGS. 2D and 2E), mimicking PTEN dysfunction via the latter's nuclear role and/or protein phosphatase activity (Chung, J. H., et al., *Cancer Res.*, 65:8096-8100 (2005)). Thus, taken together, these genetic and functional data represent strong evidence that SDHD His145Asn mutation lends susceptibility to PTEN mutation negative CS/CS-like disorders.

Figure 2E:
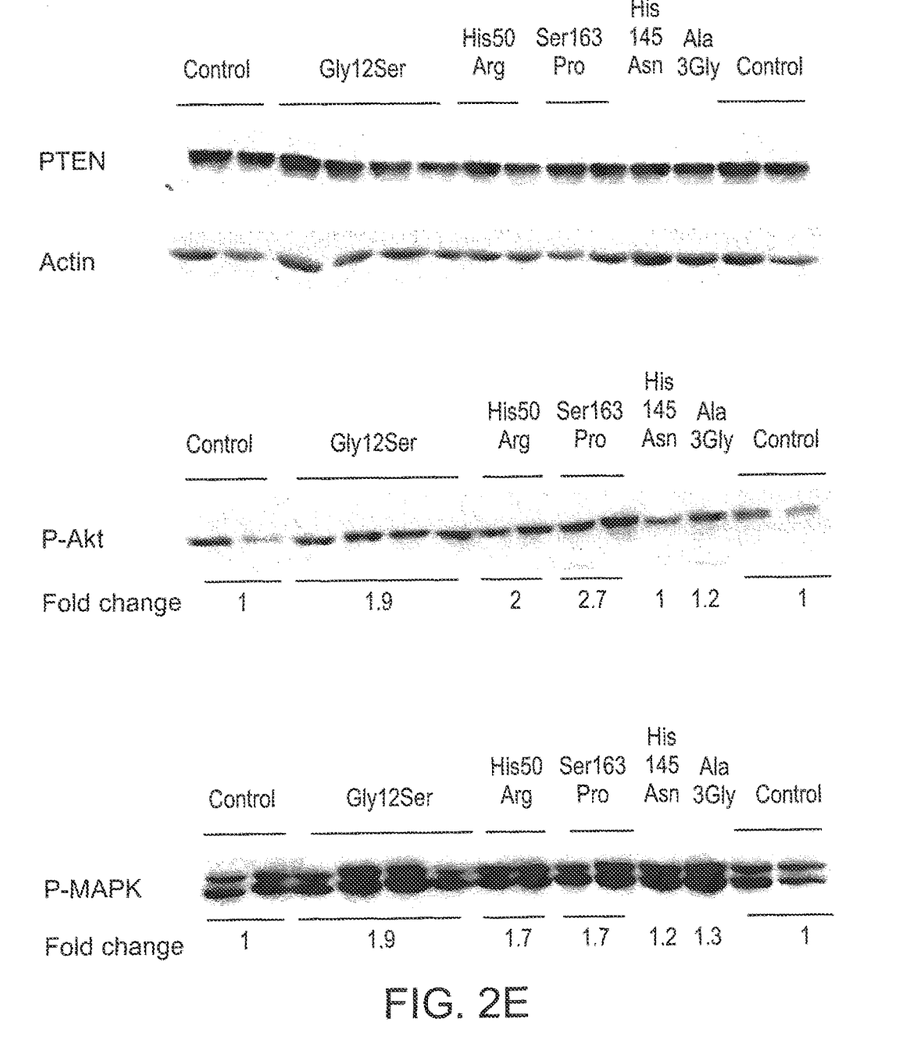
FIG. 2E shows germline protein expression of PTEN, actin (loading control), P-Akt and P-MAPK (as labeled, from top to bottom). Fold change values beneath the P-Akt and P-MAPK blots represent the mean of normalized densitometrically obtained expressional levels of patient sample(s) relative to controls. In other words, (Patient P-Akt or P-MAPK intensity/corresponding patient actin intensity)/(Control P-Akt or P-MAPK intensity/corresponding control actin intensity). The ratio of control P-Akt or P-MAPK intensity to control actin intensity was normalized to 1.0. This type of quantitation (taking the ratio of the ratios) was chosen because it results in the most conservative (i.e., under-estimated) fold changes.

The SDHB Ala3Gly variant is shown in dbSNP from the Human Genome sequencing project, but no frequency is noted. The latter usually means it is an extremely rare variant or it may be found in a non-white population. Nonetheless, our germline Ala3Gly variant occurred in a CS/CS-like individual who is white of Northern/Western European ancestry and this variant is absent in 700 normal chromosomes originating from 700 white controls of the same ancestral background. More importantly, Ala3Gly results in obvious activation of the MAPK pathway and mild activation of the AKT pathway (FIG. 2E, Table 2). It would be important to note that dot blot analysis of >700 normal controls showed that none of these control samples had increased MnSOD, increased P-MAPK or increased P-AKT (Waite, Sadler and Eng, unpublished data). Thus, the functional data strongly suggest that Ala3Gly is pathogenic and may function in a low penetrance fashion in the CS/CS-like setting.

There are human genetic reports that both support and refute SDHD Gly12Ser and His50Arg, as pathogenic (Kytola, S., et al., *Genes Chromosomes Cancer*, 34:325-332 (2002); Perren, A., et al., *Oncogene*, 21:7605-7608 (2002); Cascon, A., et al., *Genes Chromosomes Cancer*, 37:220-221 (2003)). These 2 variants have been reported to occur in 1.1-3% of Spanish population controls. His50Arg has been described in 2-3% of a French Canadian cohort as well. SDHB Ser163Pro has been described in African Americans at a 2% frequency. However, none of our 700 control chromosomes, originating from whites of Northern and Western European ancestry, were found to harbor these 3 variants (p<0.001). None of our CS/CS-like patients nor any of our controls are of Spanish, French Canadian or African ancestry. More importantly, we have shown that these 3 variants do result in increased ROS levels (Table 3, FIG. 2). Of significance to this report, moreover, Ser163Pro, His50Arg and Gly12Ser all result in activated signaling down the AKT and MAPK pathways (FIG. 2E and Table 3), mimicking PTEN dysfunction although none of these samples had PTEN alterations. Our genetic and functional data, together with recent evidence showing that most rare missense variants are deleterious (Kryukov, G. V., et al., *AJHG* epub (2007)), therefore, indicate that these 3 variants are pathogenic at least in the context of our CS/CS-like individuals, and might either be a lower penetrance allele or also signal down other unknown pathways. While we have provided genetic and strong functional evidence to show that these 3 variants are pathogenic in the CS/CS-like context, how do we explain the 1.1-3% prevalence of Gly12Ser and His50Arg in the Spanish or French Canadian populational controls and the 2% prevalence of Ser163Pro in the black population? One hypothesis is that since these are populational controls (in contrast to healthy controls), these might be individuals who have CS/CS-like phenotypes and have not been recognized given that these syndromes are extremely difficult to diagnose and more plausibly, these are individuals with partial phenotypes (i.e., formes frustes), the latter of which are quite common in the general population.

DNA from family members is not currently available for testing segregation of the mutations with clinical phenotype within families, noting that 4 individuals do not have any family history. However, maternal imprinting of SDHD (Launonen, V., et al., *proc. natl. Acad. Sci*, USA, 98:3387-3392 (2001)) and decreased penetrance of SDHB (Launonen, V., et al., *Proc. Natl. Acad. Sci, USA,* 98:3387-3392 (2001)) mutations, even in classic familial pheochromocytopenia/paraganglioma syndromes, may make this type of family analysis, especially in this present setting, much less informative. Importantly, not only do these mutations likely cause some sort of mitochondrial dysfunction as evidenced by increased expression of MnSOD and/or increased ROS, but they also show increased signaling down the PI3K-AKT and/or MAPK pathways, the latter of which car occur with pathogenic PTEN mutations as well. The reason why not all individuals found to have increased MnSOD also have germline SDHx mutations is because MnSOD levels are a broad and general (and not necessarily specific) indication of mitochondrial complex I-VI (electron transport/respiratory chain) function.

Access to the tissues or tumors for the patients with germline SDH variants and mutations was not available. However, because of the continuing lack of understanding of SDH-related carcinogenesis, it may not be helpful to look for loss of the remaining wildtype allele in tumors of these current cases. In classic SDH-related pheochromocytopenia/paraganglioma syndromes, sometimes there is somatic loss of the remaining wildtype allele accompanying the germline mutation, but retention of the wildtype allele is also observed (Baysal, B. E., et al., *Science*, 287:848-851 (2000); McWhinney, S. R., et al., *J. Clin. Endocrinol. Metab.*, 89:5694-5699 (2004)). Even more puzzling in the well-documented maternally imprinted SDHD-related tumors. With maternal imprinting, one would not expect to see loss of the remaining allele but mono-allelic expression of the mutant (paternally-transmitted) SDHD allele. In contrast, paraganglioma from germline SDHD mutation positive individuals still show clear bi-allelic SDHD expression (Baysal, B. E., et al., *Science,* 287:848-851 (2000)).

The precise mechanism leading to neoplastic transformation in patients with mutations of mitochondrial tumor suppressors is not fully understood. One hypothesis suggests that succinate, the substrate of SDH, functions as a second messenger between the mitochondria and cytosol, and inhibits the prolyl-hydroxylase enzymes, thus stabilizing HIF1 (Koivunen, P., et al., *J. Biol. Chem.*, 282:4524-4532 (2007)). This inhibition could contribute to stabilization of HIF and promote transcription of genes containing hypoxic response elements (Selak, M. A., et al., *Cancer Cell*, 7:77-85 (2005)). An alternative hypothesis is mutations in SDH result in increased ROS (Ishii, T., et al., *Cancer res.*, 65:203-209 (2005); Slane, B. G., et al., *Cancer Res.*, 66:7615-7620 (2006)). This metabolic stress results in genomic instability and accumulation of HIF1 (Ishii, T., et al., *Cancer res.*, 65:203-209 (2005)). Additionally, increased ROS levels can inactivate proteins, including PTEN, via protein oxidation (Lee, S. R., et al., *J. Biol. Chem.*, 277:20336-20342 (2002)). Because of these reports and the finding described herein that germline SDHB/D mutations/variants in CS/CS-like individuals, it was hypothesized that at least a subset of germline PTEN mutations may also lead to mitochondrial dysfunction. As proof of principle, it was found that 5 of 11 (45%) patients with germline PTEN mutations actually had over-expression of MnSOD protein in the absence of SDH mutation (Patocs and Eng, unpublished data). While the observations and the existing literature indicate interesting signaling crosstalk between the PTEN and mitochondrial signaling pathways, it is also entirely possible that SDH-related CS/CS-like phenotypes might be unrelated to the PTEN-deficient mechanism and may represent a previously undescribed syndrome.

Figure 3:
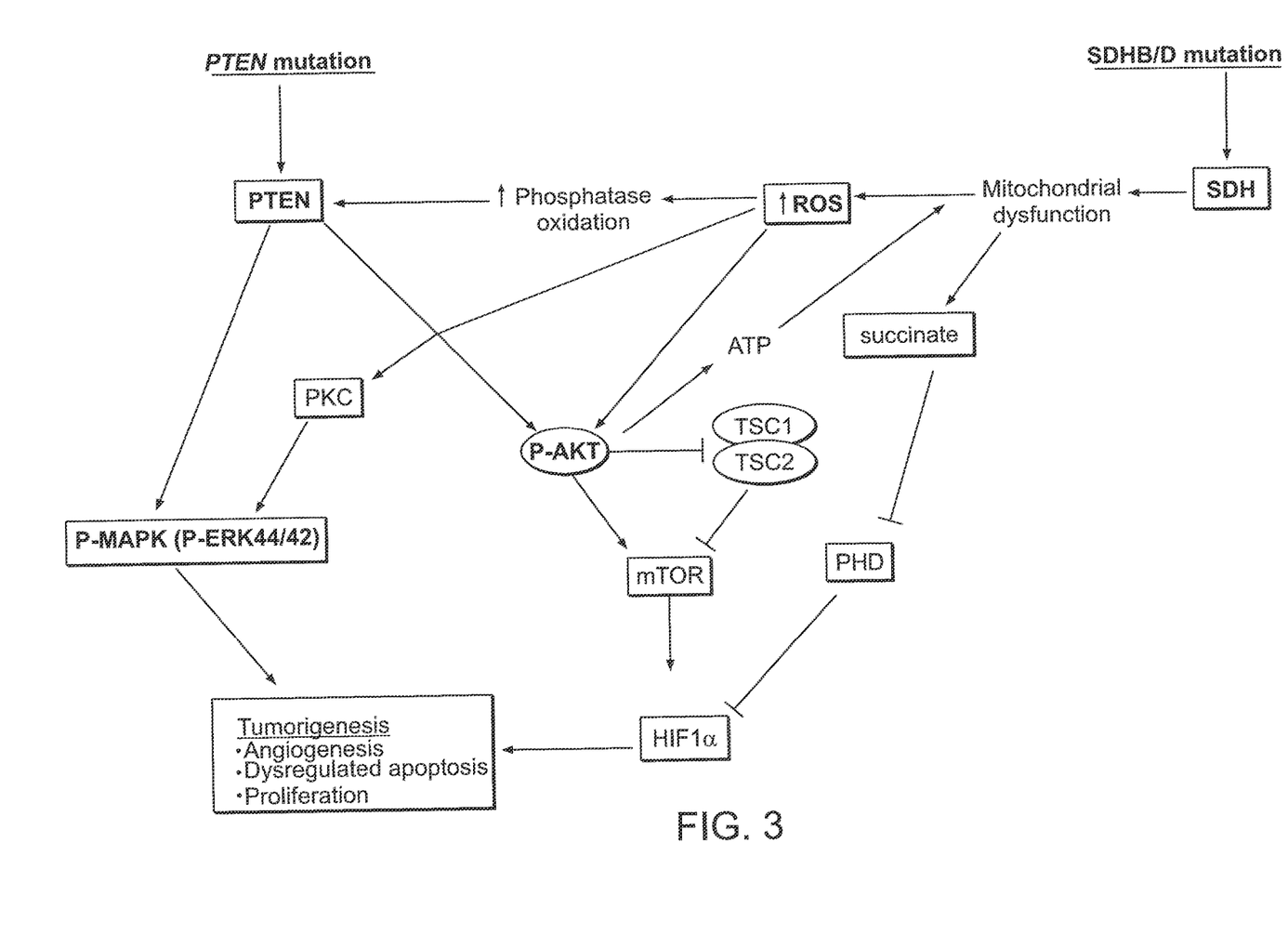

In summary, shown herein is that a subset of patients with CS or CS-like phenotypes likely has mitochondrial dysfunction irrespective of PTEN mutation status, and that this dysfunction can occur by different molecular mechanisms (FIG. 3). CS-associated SDHB or SDHD mutations may be associated with activation of similar anti-apoptotic pathways as observed with germline PTEN mutations, and that degree of mitochondrial dysfunction might differentially affect the AKT and MAPK pathways. Thus, failure of apoptosis regulation in patients, mediated by either germline PTEN or SDH mutations, resulting in mitochondrial dysfunction could be a unifying explanation for tumorigenesis in these patients (FIG. 3). Germline SDH mutation carriers have significantly higher frequencies of breast, thyroid and renal cell carcinomas compared to those with germline PTEN mutations (Table 1). It would be important to note that germline SDH mutation carriers have significantly higher frequencies of breast, thyroid and renal cell carcinomas compared to those without germline PTEN and without SDH mutations as well (Eng, unpublished data). In this study, all SDH-related thyroid cancers are papillary in contrast to PTEN-related epithelial thyroid cancers where all but one are follicular histologies. The frequencies of benign and malignant uterine disease were virtually identical between those with germline PTEN mutations and those with SDH mutations.

Figure 4:
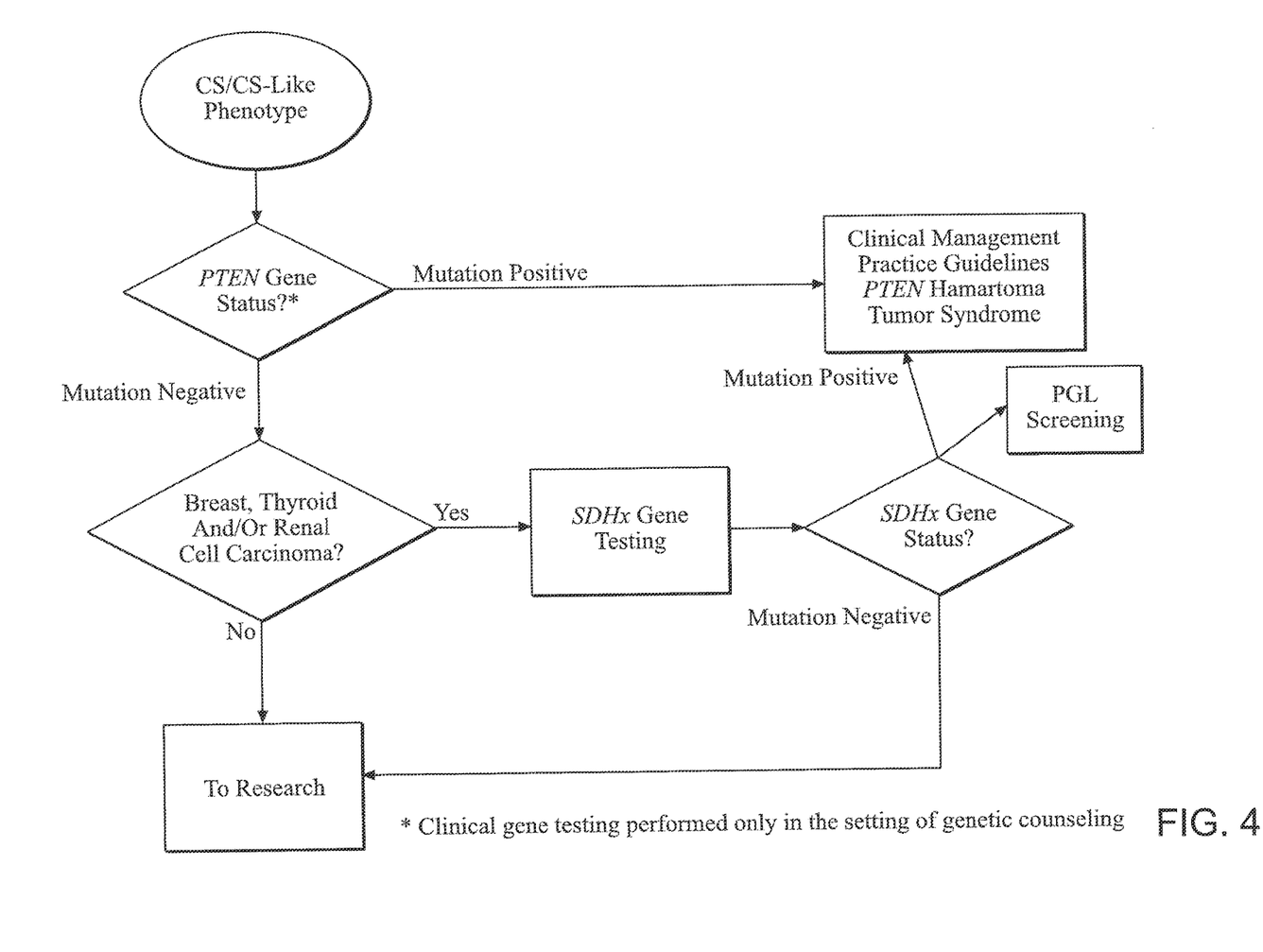
FIG. 4 shows a suggested algorithm for clinical PTEN and SDH testing for CS/CS-like individuals. Also, see text for details.

This data have important implications for both patient care and genetic counseling. Since 1997, the only susceptibility gene for CS and individuals with some neoplasias mimicking CS (CS-like) has been PTEN. Now, SDH is shown herein to be a susceptibility gene for a subset of PTEN mutation negative patients with tumors reminiscent of those component to CS. Because this study has only analyzed in detail 10 SDH mutation positive individuals with CS/CS-like features, these data should be further validated. Until then however, it appears that mutation positive CS/CS-like patients and their families have significantly increased risks of carcinomas of the breast, thyroid (especially papillary thyroid carcinoma) and kidney beyond those of PTEN-related CS. Germline PTEN mutation-negative CS/CS-like individuals should be offered SDH testing, especially in the setting of breast, papillary thyroid and/or renal carcinomas (FIG. 4). Clinicians should consider annual renal ultrasounds and PGL-type surveillance, beyond the NCCN practice guidelines for PTEN hamartoma tumor syndrome, should an individual with tumors similar to those found in CS carry a germline SDHx mutation or variant (FIG. 4).

TABLE 1

International Cowden Syndrome Consortium Operational Criteria for the Diagnosis of Cowden Syndrome (Ver. 2006)

| Pathognomonic Criteria | Major Criteria | Minor Criteria |
|---|---|---|
| Mucocutaneous lesions: Trichilemmomas, facial Acral keratoses Papillomatous papules Mucosal lesions Lhermitte-Duclos disease | Breast carcinoma Epithelial thyroid carcinoma Endometrial carcinoma Macrocephaly (say, ≥97% ile) | Other anatomic thyroid lesions Mental retardation (say, IQ ≤75) GI hamartomas Fibrocystic disease of the breast Lipomas Fibromas GU tumors or malformation |

| Operational Diagnosis in an Individual |
|---|
| 1. Mucocutaneous lesions alone if: a) there are 6 or more facial papules, of which 3 or more must be trichilemmoma, or b) cutaneous facial papules and oral mucosal papillomatosis, or c) oral mucosal papillomatosis and acral keratoses, or d) palmo plantar keratoses, 6 or more 2. 2 Major criteria but one must include macroencephaly or LDD 3. 1 Major and 3 minor criteria 4. 4 Minor criteria |

TABLE 2

Genotype and clinical phenotype for PTEN mutation negative patients with germline SDHB or SDHD mutations/variants

| Age/Sex | SDH Genotype | | Patient's Clinical Features | | | | Family History |
|---|---|---|---|---|---|---|---|
| | Gene | Mutation | Breast | Thyroid | Renal | Uterus | |
| 41F | SDHB | Ala3Gly | C | | | L | Endometrial cancer |
| 29F | SDHB | Ser163Pro | | C | | B | Breast Cancer, PTC |
| 54F | SDHB | Ser163Pro | | C | | B | Breast Cancer, PTC |
| 69F | SDHD | Gly12Ser | C | | | C | Breast Cancer, Endometrial |
| 62F | SDHD | Gly12Ser | B | B | C | L | None |
| 46F | SDHD | Gly12Ser | C | C | | L | None |
| 42F | SDHD | Gly12Ser | C | | | L | None |

TABLE 2-continued

Genotype and clinical phenotype for PTEN mutation negative patients with germline SDHB or SDHD mutations/variants

| Age/Sex | SDH Genotype | | Patient's Clinical Features | | | | Family History |
|---|---|---|---|---|---|---|---|
| | Gene | Mutation | Breast | Thyroid | Renal | Uterus | |
| 56F | SDHD | His50Arg | C | C | | | Breasat Cancer |
| 55M | SDHD | His50Arg | | C | | | Breast Cancer, PTC |
| 53F | SDHD | His145Asn | C | B | C | | None |

C carcinoma,
B benign pathology,
L uterine leiomyomas.
PTC family history of papillary thyroid carcinoma

TABLE 3

Identified Germline SDHB or SDHD mutations/variants in PTEN mutation negative CS/CS-like individuals and their functional consequences

| Mutation/Variant | MnSOD* | ROS | P-Akt Fold Change | P-MAPK Fold Change |
|---|---|---|---|---|
| SDHB Ala3Gly | Increased | Normal | 1.2 | 1.3 |
| SDHB Ser163Pro | Increased | Increased | 2.7 | 1.7 |
| SDHD Gly12Ser | Increased | Increased | 1.9 | 1.9 |
| SDHD His50Arg | Increased | Increased | 2.0 | 1.7 |
| SDHD His145Asn | Increased | Normal | 1.0 | 1.2 |

*Note patients chosen for SDH analysis were selected for increased MnSOD protein expression.

Fold change values represent the mean of normalized densitometrically obtained expressional levels of patient sample(s) relative to controls (where P-Akt/actin or P-MAPK/actin is set to 1.0), ie, a ratio of ratios.

ROS measurements were quantitated and normalized against controls (latter set at 1). The 3 mutations resulting in increased ROS had 1.5-fold over controls.

See legend to FIG. 2 for further details.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of diagnosing Cowden syndrome (CS) or CS-like syndrome in a human individual comprising
   (a) assaying protein lysates from a sample obtained from the individual with a dot blot assay to detect elevated manganese superoxide (MnSOD) protein levels;
   (b) contacting the sample comprising elevated MnSOD protein levels with PCR amplification reagents to obtain amplified DNA and directly sequencing the amplified DNA;
   (c) comparing the sequence of the SDHD gene in the amplified DNA with a control;
   (d) detecting the presence of a nucleic acid sequence in the SDHD gene that encodes an amino acid sequence comprising a Gly12Ser mutation or a His50Arg mutation; and
   (e) diagnosing CS or CS-like syndrome in the individual if at least one of the mutations is detected.

2. The method of claim 1 wherein the individual is negative for a mutated phosphatase and tensin homolog deleted on chromosome ten (PTEN).

3. The method of claim 1 wherein the individual has a carcinoma of the breast, thyroid, kidney or a combination thereof.

4. The method of claim 1 further comprising obtaining a sample from the individual.

5. A method of determining whether a human individual is at risk for developing Cowden syndrome (CS) or CS-like syndrome comprising
   (a) assaying protein lysates from the sample obtained from the PTEN mutation negative human individual with a dot blot assay to detect elevated manganese superoxide (MnSOD) protein levels;
   (b) contacting the sample comprising elevated MnSOD protein levels with PCR amplification reagents to obtain amplified DNA and directly sequencing the amplified DNA;
   (c) comparing the sequence of said SDHD gene in the amplified DNA with a control;
   (d) detecting the presence of a nucleic acid sequence in the SDHD gene that encodes an amino acid sequence comprising a Gly12Ser mutation or a His50Arg mutation; and
   (e) determining that the human individual is at risk for developing CS or CS-like syndrome if at least one of the mutations is detected.

6. The method of claim 5 wherein the individual is negative for a mutated phosphatase and tensin homolog deleted on chromosome ten (PTEN).

7. The method of claim 5 wherein the individual has a carcinoma of the breast, thyroid, kidney or a combination thereof.

8. The method of claim 5 further comprising obtaining a sample from the individual.

* * * * *